(12) United States Patent
David

(10) Patent No.: US 8,415,323 B2
(45) Date of Patent: Apr. 9, 2013

(54) MICRORNAS FOR INHIBITING VIRAL REPLICATION

(75) Inventor: Michael David, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 12/675,368

(22) PCT Filed: Aug. 27, 2008

(86) PCT No.: PCT/US2008/074513
§ 371 (c)(1),
(2), (4) Date: Jul. 23, 2010

(87) PCT Pub. No.: WO2009/029681
PCT Pub. Date: Mar. 5, 2009

(65) Prior Publication Data
US 2010/0286240 A1  Nov. 11, 2010

Related U.S. Application Data

(60) Provisional application No. 60/966,411, filed on Aug. 27, 2007.

(51) Int. Cl.
*A01N 43/04* (2006.01)
*A01N 63/00* (2006.01)
*A61K 48/00* (2006.01)
*A61K 31/70* (2006.01)

(52) U.S. Cl. ......... 514/55; 424/93.2; 435/455; 435/6.1; 514/44 A

(58) Field of Classification Search .................. None
See application file for complete search history.

(56) References Cited

U.S. PATENT DOCUMENTS 7,232,806 B2  6/2007  Tuschl et al.
7,307,067 B2  12/2007  Sarnow et al.

FOREIGN PATENT DOCUMENTS

| WO | WO-03/070750 | 8/2003 |
|---|---|---|
| WO | WO-2005/028650 | 3/2005 |
| WO | WO-2005/107816 | 11/2005 |
| WO | WO-2007/076328 | 7/2007 |

OTHER PUBLICATIONS

Randall, et al. (2007) Cellular cofactors affecting hepatits C virus infection and replication, PNAS, v.104(31):12884-9.*
Yekta, et al. (2004) MicroRNA-directed Cleavage of HOXB8 mRNA, Science, v.304:594-6.*
Elmen et al. (Apr. 17, 2008) "LNA-mediated microRNA silencing in non-human primates," Nature Letters 452:896-900.
Gao et al. (Aug. 7, 2008) "Inhibition of hepatitis B virus gene expression and replication by artificial microRNA," World J Gastroenterol 14(29):4684-4689.
Gondeau et al. (2009). "Cellular models for the screening and development of anti-hepatitis C virus agents," Pharmacol Thera 124:1-22.
Gottwein and Bukh (Aug. 14, 2007) "Hepatitis C virus-host cell interactions uncovered," PNAS 104(33):13215-13216.
Gramantieri et al. (Jul. 1, 2007) "Cyclin G1 is a target of miR-122a, a microRNA frequently down-regulated in human hepatocellular carcinoma," Cancer Res 67(13):6092-6099.
Jopling et al. (Sep. 2, 2005) "Modulation of hepatitis C virus RNA abundance by a liver-specific microRNA," Science 309:1577-1581.
Kumar (Feb. 1, 2008) "RNA interference: a multifaceted innate antiviral defense," Retrovirol 5:17 (4 pages).
Lecellier et al. (Apr. 22, 2005) "A cellular microRNA mediates antiviral defense in human cells," Science 308:557-559.
Liu et al. (Jun. 29, 2004) "An oligonucleotide microchip for genome-wide microRNA profiling in human and mouse tissues," PNAS 101(26):9740-9744.
Lupberger et al. (2008) "RNAi—a powerful tool to unravel hepatitis C virus-host interactions within the infectious life cycle," J Hepatol 48:523-525.
Pan et al. (Sep. 7, 2007) "New therapeutic opportunities for Hepatitis C based on small RNA," World J Gastroenterol 13(33):4431-4436.
Pedersen et al.(Oct. 18, 2007) "Interferon modulation of cellular microRNAs as an antiviral mechanism," Nature Letters 449:919-923.
Pedersen and David (2008) "MicroRNAs in the immune response," Cytokine 43(3):391-394.
Randall et al. (Jul. 31, 2007) "Cellular cofactors affecting hepatitis C virus infection and replication," PNAS 14(31):12884-12889.
Scaria et al. (Oct. 11, 2006) "Host-virus interaction: a new role for microRNAs," Retrovirol 3:68 (9 pages).
Zhong et al. (Jun. 28, 2005). "Robust hepatitis C virus infection in vitro," PNAS 102(26):9294-9299.

* cited by examiner

*Primary Examiner* — Jennifer Pitrak McDonald
(74) *Attorney, Agent, or Firm* — Morrison & Foerster LLP

(57) ABSTRACT

The present invention relates to reducing accumulation of viral genomes in a target cell. In particular the present invention provides compositions and methods for combating viral infection through RNA interference. Specifically the present invention provides cellular microRNA mimics for treating virus-infected subjects.

12 Claims, 9 Drawing Sheets

E1

E2

Figure 5 Interferon Up-Regulated Cellular MicroRNAs

| up regulated miRs | SEQUENCE | SEQ ID |
|---|---|---|
| mmu-mir-351 | UCCCUGAGGAGCCCUUUGAGCCUG | SEQ ID NO: 9 |
| mmu-mir-466 | AUACAUACACGCACACAUAAGAC | SEQ ID NO: 16 |
| mmu-mir-431 | UGUCUUGCAGGCCGUCAUGCAGG | SEQ ID NO: 10 |
| mmu-mir-196b | UAGGUAGUUUCCUGUUGUUGG | SEQ ID NO: 7 |
| mmu-mir-18 | UAAGGUGCAUCUAGUGCAGAUA | SEQ ID NO: 17 |
| mmu-mir-297 | AUGUAUGUGUGCAUGUGCAUG | SEQ ID NO: 18 |
| mmu-mir-26a | UUCAAGUAAUCCAGGAUAGGC | SEQ ID NO: 19 |
| mmu-mir-466 | AUACAUACACGCACACAUAAGAC | SEQ ID NO: 20 |
| mmu-mir-449 | UGGCAGUGUAUUGUUAGCUGGU | SEQ ID NO: 21 |
| mmu-mir-133a | UUGGUCCCCUUCAACCAGCUGU | SEQ ID NO: 22 |
| mmu-mir-1 | UGGAAUGUAAAGAAGUAUGUA | SEQ ID NO: 1 |
| mmu-mir-136 | ACUCCAUUUGUUUUGAUGAUGGA | SEQ ID NO: 23 |
| mmu-mir-448 | UUGCAUAUGUAGGAUGUCCCAU | SEQ ID NO: 11 |
| mmu-mir-295 | AAAGUGCUACUACUUUUGAGUCU | SEQ ID NO: 24 |
| mmu-mir-96 | UUUGGCACUAGCACAUUUUUGCU | SEQ ID NO: 25 |
| mmu-mir-126 (3p/5p) | UCGUACCGUGAGUAAUAAUGC/CAUUAUUACUUUUGGUACGCG | SEQ ID NO: 26 / SEQ ID NO: 27 |
| mmu-mir-300 | UAUGCAAGGGCAAGCUCUCUUC | SEQ ID NO: 28 |
| mmu-mir-467 (a/b) | AUAUACAUACACACACCUACAC/AUAUACAUACACACACCAACAC | SEQ ID NO: 29 / SEQ ID NO: 30 |
| mmu-mir-29a | UAGCACCAUCUGAAAUCGGUU | SEQ ID NO: 31 |
| mmu-mir-181b | AACAUUCAUUGCUGUCGGUGGG | SEQ ID NO: 32 |
| mmu-mir-34b | UAGGCAGUGUAAUUAGCUGAUUG | SEQ ID NO: 33 |
| mmu-mir-295 | AAAGUGCUACUACUUUUGAGUCU | SEQ ID NO: 34 |
| mmu-mir-7b | UGGAAGACUUGUGAUUUUGUU | SEQ ID NO: 35 |
| mmu-mir-409 | GAAUGUUGCUCGGUGAACCCCUU | SEQ ID NO: 36 |
| mmu-mir-224 | UAAGUCACUAGUGGUUCCGUUUA | SEQ ID NO: 37 |
| mmu-mir-342 | UCUCACACAGAAAUCGCACCCGUC | SEQ ID NO: 38 |
| mmu-mir-26a | UUCAAGUAAUCCAGGAUAGGC | SEQ ID NO: 39 |
| mmu-mir-341 | UCGAUCGGUCGGUCGGUCAGU | SEQ ID NO: 40 |
| mmu-mir-33 | GUGCAUUGUAGUUGCAUUG | SEQ ID NO: 41 |
| mmu-mir-299 | UGGUUUACCGUCCCACAUACAU | SEQ ID NO: 42 |
| mmu-mir-302 | UAAGUGCUUCCAUGUUUUGGUGA | SEQ ID NO: 43 |
| mmu-mir-135a | UAUGGCUUUUUAUUCCUAUGUGA | SEQ ID NO: 44 |
| mmu-mir-375 | UUUGUUCGUUCGGCUCGCGUGA | SEQ ID NO: 45 |
| mmu-mir-124a | UAAGGCACGCGGUGAAUGCC | SEQ ID NO: 46 |
| mmu-mir-135a | UAUGGCUUUUUAUUCCUAUGUGA | SEQ ID NO: 47 |
| mmu-mir-186 | CAAAGAAUUCUCCUUUUGGGCUU | SEQ ID NO: 48 |
| mmu-mir-199b | CCCAGUGUUUAGACUACCUGUUC | SEQ ID NO: 49 |
| mmu-mir-410 | AAUAUAACACAGAUGGCCUGUU | SEQ ID NO: 50 |
| mmu-mir-128a | UCACAGUGAACCGGUCUCUUUU | SEQ ID NO: 51 |
| mmu-mir-148a | UCAGUGCACUACAGAACUUUGU | SEQ ID NO: 52 |
| mmu-mir-376b | AUCAUAGAGGAACAUCCACUUU | SEQ ID NO: 53 |
| mmu-mir-412 | ACUUCACCUGGUCCACUAGCCGU | SEQ ID NO: 54 |
| mmu-mir-196a | UAGGUAGUUUCAUGUUGUUGG | SEQ ID NO: 55 |
| mmu-mir-219 | UGAUUGUCCAAACGCAAUUCU | SEQ ID NO: 56 |
| mmu-mir-337 | UUCAGCUCCUAUAUGAUGCCUUU | SEQ ID NO: 57 |
| mmu-mir-345 | UGCUGACCCCUAGUCCAGUGC | SEQ ID NO: 58 |
| mmu-mir-30c | UGUAAACAUCCUACACUCUCAGC | SEQ ID NO: 2 |
| mmu-mir-451 | AAACCGUUACCAUUACUGAGUU | SEQ ID NO: 59 |
| mmu-mir-425 | AUCGGGAAUGUCGUGUCCGCC | SEQ ID NO: 60 |
| mmu-mir-31 | AGGCAAGAUGCUGGCAUAGCUG | SEQ ID NO: 61 |
| mmu-mir-383 | AGAUCAGAAGGUGACUGUGGCU | SEQ ID NO: 62 |
| mmu-mir-138 | AGCUGGUGUUGUGAAUC | SEQ ID NO: 63 |
| mmu-mir-148b | UCAGUGCAUCACAGAACUUUGU | SEQ ID NO: 64 |
| mmu-mir-335 | UCAAGAGCAAUAACGAAAAAUGU | SEQ ID NO: 65 |

Figure 6 Interferon Down-Regulated Cellular MicroRNAs

| down regulated miRs | SEQUENCE | SEQ ID |
|---|---|---|
| mmu-mir-129 (3p/5p) | AAGCCCUUACCCCAAAAAGCAU/CUUUUUGCGGUCUGGGCUUGCU | SEQ ID NO: 66 / SEQ ID NO: 67 |
| mmu-mir-128b | UCACAGUGAACCGGUCUCUUUC | SEQ ID NO: 5 |
| mmu-mir-29b | UAGCACCAUUUGAAAUCAGUGUU | SEQ ID NO: 68 |
| mmu-mir-340 | UCCGUCUCAGUUACUUUAUAGCC | SEQ ID NO: 69 |
| mmu-mir-29a | UAGCACCAUCUGAAAUCGGUU | SEQ ID NO: 70 |
| mmu-mir-124a | UAAGGCACGCGGUGAAUGCC | SEQ ID NO: 71 |
| mmu-mir-21 | UAGCUUAUCAGACUGAUGUUGA | SEQ ID NO: 72 |
| mmu-mir-125b | UCCCUGAGACCCUAACUUGUGA | SEQ ID NO: 4 |
| mmu-mir-29c | UAGCACCAUUUGAAAUCGGU | SEQ ID NO: 73 |
| mmu-mir-98 | UGAGGUAGUAAGUUGUAUUGUU | SEQ ID NO: 74 |
| mmu-mir-181b | AACAUUCAUUGCUGUCGGUGGG | SEQ ID NO: 75 |
| mmu-mir-377 | AUCACACAAAGGCAACUUUUGU | SEQ ID NO: 76 |
| mmu-mir-19a | UGUGCAAAUCUAUGCAAAACUGA | SEQ ID NO: 77 |
| mmu-mir-325 | CCUAGUAGGUGCUCAGUAAGUGU | SEQ ID NO: 78 |
| mmu-mir-31 | AGGCAAGAUGCUGGCAUAGCUG | SEQ ID NO: 79 |
| mmu-mir-381 | UAUACAAGGGCAAGCUCUCUGU | SEQ ID NO: 80 |
| mmu-mir-425 | AUCGGGAAUGUCGUGUCCGCC | SEQ ID NO: 81 |
| mmu-mir-299 | UGGUUUACCGUCCCACAUACAU | SEQ ID NO: 82 |
| mmu-mir-28 | AAGGAGCUCACAGUCUAUUGAG | SEQ ID NO: 83 |
| mmu-mir-20 (a/b) | UAAAGUGCUUAUAGUGCAGGUAG/CAAAGUGCUCAUAGUGCAGGUA | SEQ ID NO: 84 / SEQ ID NO: 85 |
| mmu-mir-26a | UUCAAGUAAUCCAGGAUAGGC | SEQ ID NO: 86 |
| mmu-mir-106a (5p/3p) | CAUUAUUACUUUUGGUACGCG/UCGUACCGUGAGUAAUAAUGC | SEQ ID NO: 87 / SEQ ID NO: 88 |
| mmu-mir-93 | CAAAGUGCUGUUCGUGCAGGUAG | SEQ ID NO: 89 |
| mmu-mir-7a | UGAGGUAGUAGGUUGUAUAGU | SEQ ID NO: 90 |
| mmu-mir-106b | UAAAGUGCUGACAGUGCAGAU | SEQ ID NO: 91 |
| mmu-mir-130b | CAGUGCAAUGAUGAAAGGGCAU | SEQ ID NO: 92 |
| mmu-mir-30c | UGUAAACAUCCUACACUCUCAGC | SEQ ID NO: 93 |
| mmu-mir-30d | UGUAAACAUCCCCGACUGGAAG | SEQ ID NO: 94 |
| mmu-mir-200b | UAAUACUGCCUGGUAAUGAUGAC | SEQ ID NO: 95 |
| mmu-mir-33 | GUGCAUUGUAGUUGCAUUG | SEQ ID NO: 96 |
| mmu-mir-16 | UAGCAGCACGUAAAUAUUGGCG | SEQ ID NO: 97 |
| mmu-mir-7f | UGAGGUAGUAGAUUGUAUAGU | SEQ ID NO: 98 |
| mmu-mir-15b | UAGCAGCACAUCAUGGUUUACA | SEQ ID NO: 99 |
| mmu-mir-451 | AAACCGUUACCAUUACUGAGUU | SEQ ID NO: 100 |
| mmu-mir-15a | UAGCAGCACAUAAUGGUUUGUG | SEQ ID NO: 101 |
| mmu-mir-103 | AGCAGCAUUGUACAGGGCUAUGA | SEQ ID NO: 102 |
| mmu-mir-19a | UGUGCAAAUCUAUGCAAAACUGA | SEQ ID NO: 103 |
| mmu-mir-376a | AUCGUAGAGGAAAAUCCACGU | SEQ ID NO: 104 |
| mmu-mir-294 | AAAGUGCUUCCCUUUUGUGUGU | SEQ ID NO: 105 |
| mmu-mir-135a | UAUGGCUUUUUAUUCCUAUGUGA | SEQ ID NO: 106 |
| mmu-mir-409 | GAAUGUUGCUCGGUGAACCCCUU | SEQ ID NO: 107 |
| mmu-mir-139 | UCUACAGUGCACGUGUCU | SEQ ID NO: 108 |
| mmu-mir-291 | CAUCAAAGUGGAGGCCCUCUCU | SEQ ID NO: 109 |
| mmu-mir-23a | AUCACAUUGCCAGGGAUUUCC | SEQ ID NO: 110 |
| mmu-mir-434-3p | UUUGAACCAUCACUCGACUCC | SEQ ID NO: 111 |
| mmu-mir-486 | UCCUGUACUGAGCUGCCCCGAG | SEQ ID NO: 112 |
| mmu-mir-10a | UACCCUGUAGAUCCGAAUUUGUG | SEQ ID NO: 113 |
| mmu-mir-219 | UGAUUGUCCAAACGCAAUUCU | SEQ ID NO: 114 |
| mmu-mir-382 | GAAGUUGUUCGUGGUGGAUUCG | SEQ ID NO: 115 |
| mmu-mir-107 | AGCAGCAUUGUACAGGGCUAUCA | SEQ ID NO: 116 |

Figure 6 (Continued)

| down regulated miRs | SEQUENCE | SEQ ID |
|---|---|---|
| mmu-mir-133b | UUGGUCCCCUUCAACCAGCUA | SEQ ID NO: 117 |
| mmu-mir-378 | CUCCUGACUCCAGGUCCUGUGU | SEQ ID NO: 118 |
| mmu-mir-7b | UGAGGUAGUAGGUUGUGUGGUU | SEQ ID NO: 119 |
| mmu-mir-34a | UGGCAGUGUCUUAGCUGGUUGUU | SEQ ID NO: 120 |
| mmu-mir-200c | UAAUACUGCCGGGUAAUGAUGG | SEQ ID NO: 121 |
| mmu-mir-342 | UCUCACACAGAAAUCGCACCCGUC | SEQ ID NO: 122 |
| mmu-mir-7d | AGAGGUAGUAGGUUGCAUAGU | SEQ ID NO: 123 |
| mmu-mir-30d | UGUAAACAUCCCCGACUGGAAG | SEQ ID NO: 124 |
| mmu-mir-146 | UGAGAACUGAAUUCCAUGGGUU | SEQ ID NO: 125 |
| mir-122 | UGGAGUGUGACAAUGGUGUUUGU | SEQ ID NO: 3 |

US 8,415,323 B2

MICRORNAS FOR INHIBITING VIRAL REPLICATION

CROSS-REFERENCE TO RELATED APPLICATIONS

This is a U.S. National Phase of International Application No. PCT/US2008/074513, filed Aug. 27, 2008, which claims benefit of U.S. Provisional Application No. 60/966,411 filed Aug. 27, 2007, all of which are herein incorporated by reference in their entirety.

This invention was made with government support under CA80105 awarded by National Institute of Health. The government has certain rights in the invention.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 643882000400SEQLIST.txt, date recorded: Jun. 22, 2010, size: 23 KB).

FIELD OF THE INVENTION

The present invention relates to reducing accumulation of viral genomes in a target cell. In particular the present invention provides compositions and methods for combating viral infection through RNA interference. Specifically the present invention provides cellular microRNA mimics for treating virus-infected cells.

BACKGROUND OF THE INVENTION

Hepatitis C virus (HCV), a member of the Flaviviridae family, contains a positive single-stranded RNA genome that also functions as mRNA. Approximately 4 million persons in the United States and probably more than 100 million people worldwide are infected with hepatitis C virus (HCV). The virus has the unique ability to cause persistent infection in susceptible hosts after parenteral or percutaneous transmission. The immunologic correlates of protection and viral clearance and the pathogenesis of liver injury are yet to be defined. Nearly 70% to 80% of infected persons become chronic carriers, and chronic and progressive HCV infection carries significant morbidity and mortality (e.g., major cause of cirrhosis, end-stage liver disease, and liver cancer).

Currently, the only approved therapy for treatment of chronic HCV infection is a 24-48 week course of the combination of type I interferon (IFNα/β) and ribavirin with sustained viral clearance observed in 42% to 82% of treated individuals. Unfortunately this treatment is problematic due to considerable deleterious side effects. Ribavirin causes dose-related hemolysis and anemia, with severe side effects frequently observed with combination therapy. In many cases, treatment has to be reduced to mono-therapy with interferon alone.

The mechanism(s) of actions of IFN (or resistance to IFN) during antiviral therapy for HCV and other RNA viruses are not well understood, although such an understanding is desirable to guide development of new antiviral treatments.

SUMMARY OF THE INVENTION

The present invention relates to reducing accumulation of viral genomes in a target cell. In particular the present invention provides compositions and methods for combating viral infection through RNA interference. Specifically the present invention provides cellular microRNA mimics for treating virus-infected cells.

The present invention provides methods for reducing accumulation of Hepatitis C virus (HCV) RNA in a target cell, the method comprising: introducing a first isolated nucleic acid molecule into a Hepatitis C virus (HCV)-infected target cell under conditions suitable (e.g., in an amount effective) for reducing accumulation of HCV RNA in the target cell, wherein the first isolated nucleic acid molecule comprises the nucleotide sequence of a cellular microRNA selected from the group consisting of miR-196, miR-296, miR-351, miR-431 and miR-448. In some embodiments, the cellular microRNA is a murine microRNA selected from the group consisting of miR-196, miR-296, miR-351, miR-431, and miR-448 while in other embodiments, the cellular microRNA is a human homolog of the murine microRNA. In some embodiments, the cellular microRNA comprises one of the group consisting of a mature microRNA, a pre-microRNA, and a seed sequence of the mature microRNA (e.g., 5' residues 2 to 7 or 2 to 8 of the mature microRNA). In some embodiments, the cellular microRNA is the miR-196 consisting of the nucleotide sequence set forth as SEQ ID NO:7, the miR-296 consisting of the nucleotide sequence set forth as SEQ ID NO:8, the cellular microRNA is the miR-351 consisting of the nucleotide sequence set forth as SEQ ID NO:9, the miR-431 consisting of the nucleotide sequence set forth as SEQ ID NO:10 or the miR-448 consisting of the nucleotide sequence set forth as SEQ ID NO:11. In some preferred embodiments, the methods further comprise introducing a second isolated nucleic acid molecule into the HCV-infected target cell, wherein the second isolated nucleic acid molecule comprises the nucleotide sequence complementary to miR-122. In some embodiments, the miR-122 consists of the nucleotide sequence set forth as SEQ ID NO:3. In further embodiments, the cellular microRNA comprises the miR-196, the miR-296, the miR-351, the miR-431 and the miR-448. In some embodiments, one or both of the first and second nucleic acids are part of a composition further comprising one of the group consisting of a cationic lipid, a neutral lipid, and polyethylene glycol (PEG). In some embodiments one or both of the first and second nucleic acids are modified with cholesterol. In alternative embodiments, one or both of the first and second nucleic acids are contained within an expression vector. In some embodiments, the methods of the present invention reduce HCV replication in an infected target cell. In some preferred embodiments, the target cell is a hepatocyte. In some embodiments, the target cell is in vitro, while in other embodiments the target cell is in vivo. In some preferred embodiments, the methods comprise administering one or both of the first and second isolated nucleic acid molecules to a subject comprising the HCV-infected target cell. Some methods further comprise treating the subject for an HCV mediated disease condition. In some embodiments, the methods further comprise administering one or both of a type I interferon (e.g., IFN-alpha or IFN-beta) and ribavarin.

In addition, the present invention provides compositions comprising: an isolated nucleic acid molecule consisting of the nucleotide sequence of one of the group consisting of SEQ ID NO:7, SEQ ID NO:8, SEQ ID NO:9, SEQ ID NO:10 and SEQ ID NO:11; and a pharmaceutically acceptable delivery vehicle. The present invention also provides compositions comprising: an isolated nucleic acid molecule consisting of 18 to 25 nucleotides having a nucleotide sequence identity of at least 90% to one of the group consisting of SEQ ID NO:7, SEQ ID NO:8, SEQ ID NO:9, SEQ ID NO:10 and SEQ ID NO:11; and a pharmaceutically acceptable delivery vehicle. In some preferred embodiments, the nucleic acid molecule is a miRNA. In some embodiments, the nucleic acid molecule is single-stranded, while in others the nucleic acid molecule is at least partially double-stranded. In some embodiments, the nucleic acid molecule is selected from the group consisting of RNA, DNA and modified nucleotide molecules. In some preferred embodiments, the nucleic acid molecule is comprised within an expression vector.

Moreover, the present invention provides kits comprising: an isolated nucleic acid molecule comprising the nucleotide sequence of a cellular microRNA selected from the group consisting of miR-196, miR-296, miR-351, miR-431 and miR-448; and instructions for use in practicing methods comprising: introducing said isolated nucleic acid molecule into a Hepatitis C virus (HCV)-infected target cell under conditions suitable (e.g., nucleic acid in an amount effective) for reducing accumulation of HCV RNA in the target cell. In some embodiments, the kit further comprises a pharmaceutically acceptable delivery vehicle for the isolated nucleic acid molecule.

Also provided by the present invention are methods comprising: introducing an isolated nucleic acid molecule into a virus-infected target cell under conditions suitable (e.g., nucleic acid in an amount effective) for reducing accumulation of viral nucleic acid in the target cell, wherein the isolated nucleic acid molecule comprises the nucleotide sequence of an interferon up-regulated cellular microRNA. In some embodiments, the interferon up-regulated cellular microRNA is selected from the group consisting of the nucleotide sequences of FIG. 5. In some embodiments, the virus is an RNA virus. In some preferred embodiments, the RNA virus is selected from the group consisting of Hepatitis C virus (HCV), dengue virus, human immunodeficiency virus (HIV), and influenza virus. Compositions and kits for practicing the methods of the present invention are provided as well.

In still further embodiments, the present invention provides method comprising: introducing an isolated nucleic acid molecule into a virus-infected target cell under conditions suitable (e.g., nucleic acid in an amount effective) for reducing accumulation of viral nucleic acid in the target cell, wherein the isolated nucleic acid molecule comprises the reverse complement nucleotide sequence of an interferon down-regulated cellular microRNA. In some embodiments, the interferon down-regulated cellular microRNA is selected from the group consisting of the nucleotide sequences of FIG. 6. In some preferred embodiments, the RNA virus is selected from the group consisting of Hepatitis C virus (HCV), dengue virus, human immunodeficiency virus (HIV), and influenza virus. Compositions and kits for practicing the methods of the present invention are provided as well.

Additionally, the present invention provides methods comprising: introducing an isolated nucleic acid molecule into a target cell, wherein the isolated nucleic acid molecule comprises the nucleotide sequence of an interferon-modulated cellular microRNA. In some embodiments, the interferon modulated cellular microRNA is an interferon up-regulated cellular microRNA selected from the group consisting of the nucleotide sequences of FIG. 5. In other embodiments, the interferon modulated cellular microRNA is an interferon down-regulated cellular microRNA selected from the group consisting of the nucleotide sequences of FIG. 6.

In some embodiments, the methods of the present invention establish a type I interferon-treated state in the target cell (e.g., state in which at least one cellular microRNA is modulated up or down regulated modulated in a manner resembling treatment of the target cell with a type I interferon (e.g., up or down regulated in direction if not magnitude as shown in FIG. 5 or FIG. 6). In some embodiments, the cellular microRNA is a murine microRNA, while in other embodiments the cellular microRNA is a human homolog of the murine microRNA. In some embodiments, the cellular microRNA comprises one of the group consisting of a mature microRNA, a pre-microRNA, and a seed sequence of the mature microRNA (e.g., 5' residues 2 to 7 or 2 to 8 of the mature microRNA). In some embodiments, the cellular microRNA comprises a plurality of microRNAs (e.g., 2, 3, 4, 5 or more). In some preferred embodiments, the target cell is a hepatocyte. In some embodiments, the target cell is in vitro, while in other embodiments the target cell is in vivo.

BRIEF DESCRIPTION OF THE DRAWINGS

FIG. 5 provides a listing of the interferon up-regulated cellular miRs identified during development of the present invention.

FIG. 6 provides a listing of the interferon down-regulated cellular miRs identified during development of the present invention.

GENERAL DESCRIPTION OF THE INVENTION

Figure 1:
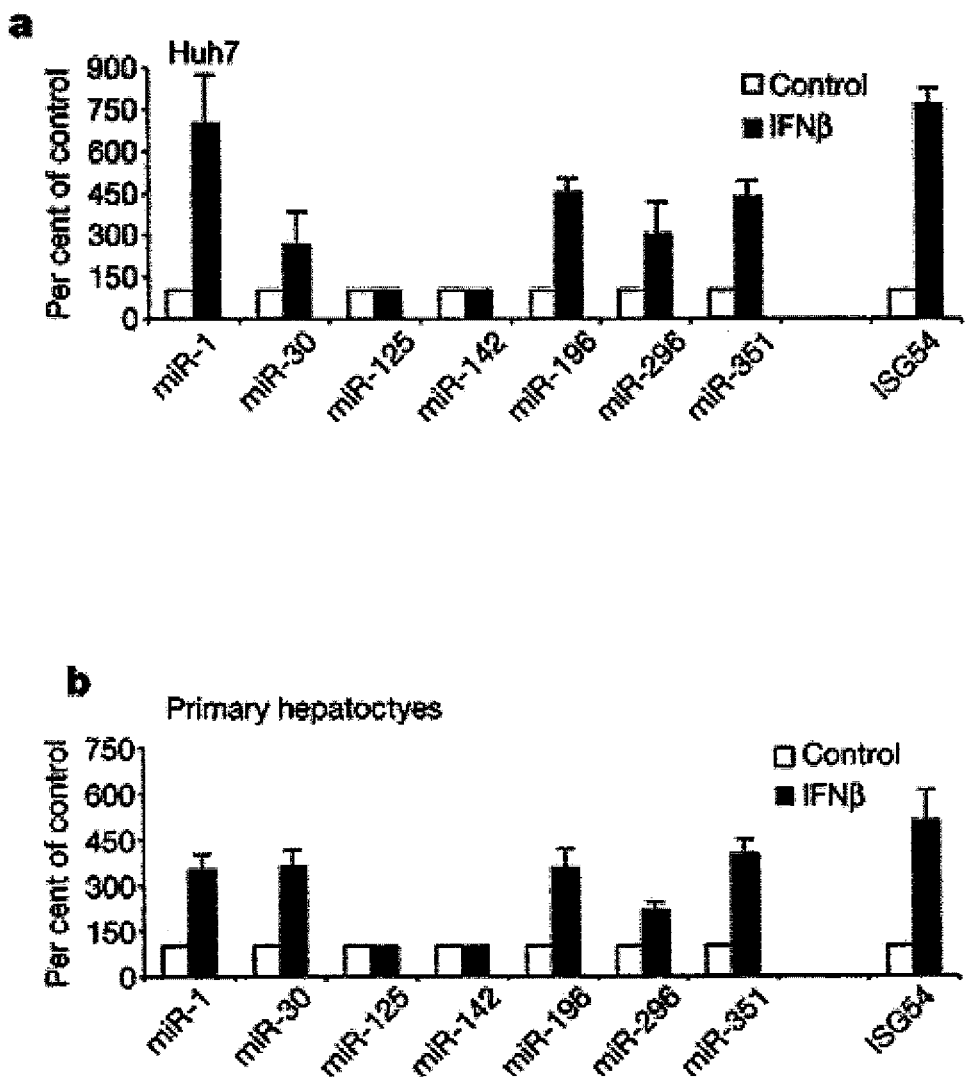
FIGS. 1A-E show regulation of miR expression by IFNβ in Huh7 cells and primary hepatocytes. Huh7 cells a, or primary hepatocytes b, were stimulated with 100 U/ml IFNβ for 2 hrs, and levels of the indicated miRs were quantitated by real-time PCR. ISG54 induction is shown for comparison. c, Time course of miR induction by IFNβ: Huh7 cells were stimulated with 100 U/ml IFNβ for the indicated times, and miR-1, miR-196 or ISG54 expression levels were quantitated by real-time PCR. d, Dose-response analysis of miR induction by IFNβ: Huh7 cells were stimulated with the indicated doses of IFNβ for 2 hours, and miR-1, miR-196 or ISG54 expression levels were quantitated by real-time PCR. e, Time course and dose-response analysis of miR-122 down-regulation by IFNβ: Huh7 cells were stimulated as described in (c) and (d), and miR-122 levels were quantitated by real-time PCR. Bars represent means+/−std of at least four independent experiments.
Figure 1:
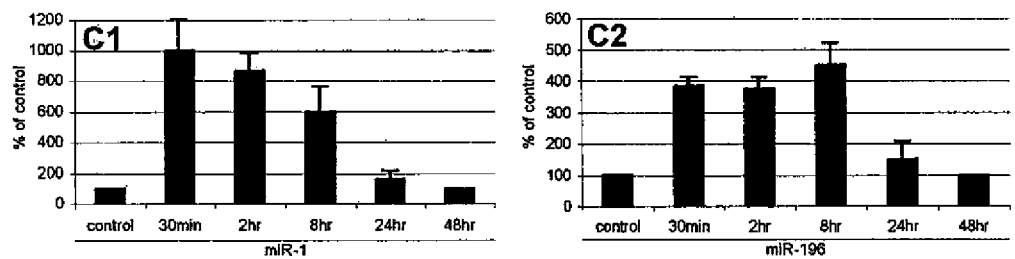
Figure 1:
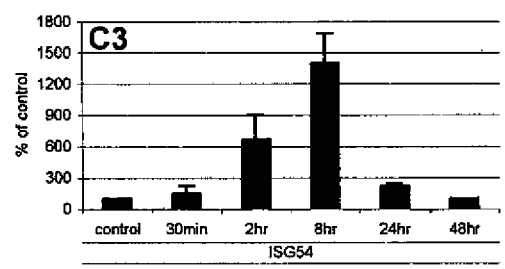
Figure 1:
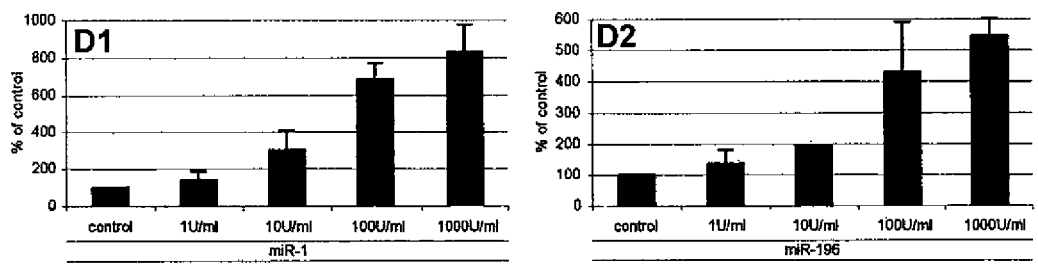
Figure 1:
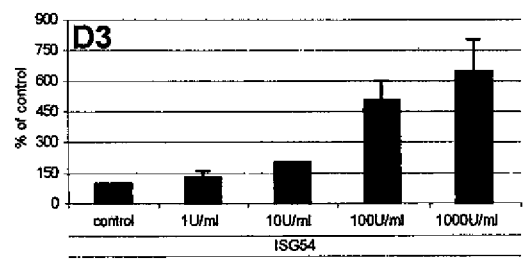
Figure 1:
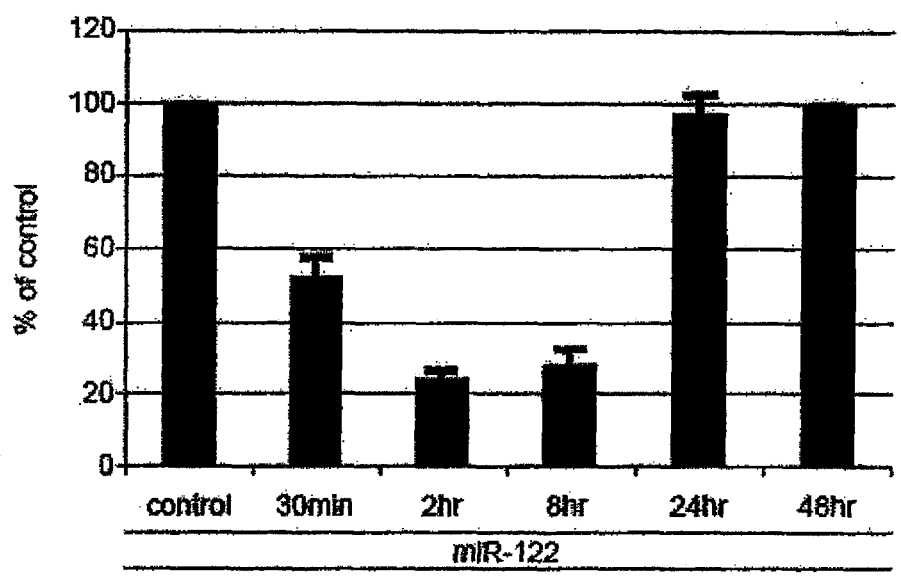
Figure 1:
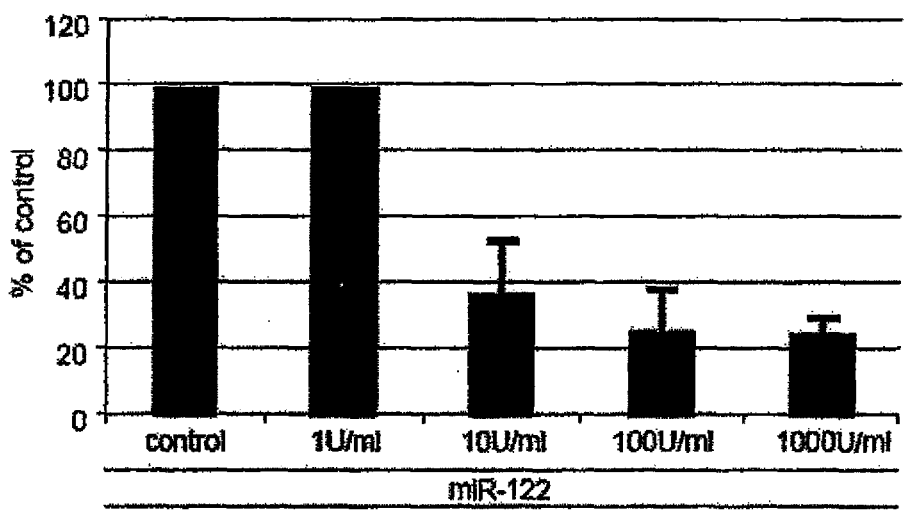

RNA interference through non-coding microRNAs (miRs) represents a vital component of the innate antiviral immune response in plants and invertebrate animals, however, a role for cellular miRs in the defense against viral infection in mammalian organisms has thus far remained elusive[1]. As determined during development of the present invention, interferon beta (IFNβ) rapidly modulates the expression of numerous cellular miRs, with eight of these IFNβ-induced miRs having sequence-predicted targets within the hepatitis C virus (HCV) genomic RNA. Introduction of synthetic miR-mimics corresponding to these IFNβ-induced miRs reproduces the antiviral effects of IFNβ on HCV replication and infection, whereas neutralization of these antiviral miRs with anti-miRs reduces the antiviral effects of IFN against HCV.

In addition, during development of the present invention, IFNβ treatment was found to lead to a significant reduction in the expression of the liver-specific miR-122, a miR that has been previously shown to be essential for HCV replication[2]. Thus mammalian cells like plant and invertebrate cells, utilize cellular miRs to combat viral infections. Accordingly, the present invention provides compositions and methods comprising cellular miR mimics for inhibiting viral replication.

DETAILED DESCRIPTION OF THE INVENTION

The present invention relates to reducing accumulation of viral genomes in a target cell. In particular the present invention provides compositions and methods for combating viral infection through RNA interference. Specifically the present invention provides cellular microRNA mimics for treating virus-infected cells.

I. Methods

The present invention provides methods of reducing the amount of a viral genome in a target cell, where the target cell may be present in vitro or in vivo. The term "reducing the amount of" indicates that the level or quantity of the viral genome in the target cell is reduced by at least about 2-fold, usually by at least about 5-fold (e.g., 10-fold, 15-fold, 20-fold, 50-fold, or 100-fold or more) as compared to a control (e.g., an untreated target cell).

In practicing the subject methods, an effective amount of a miRNA (microRNA) mimic is introduced into the target cell, where any convenient protocol for introducing the agent into the target cell may be employed. The miRNA mimic is an agent that reproduces the antiviral effects of IFNβ-induced cellular miRNAs in the target cell. As is known in the art, miRNAs are single stranded RNA molecules that range in length from about 20 to about 25 nt (e.g., 20, 21, 22, 23, 24 or 25 nt). The miRNA mimics may or may not be completely complementary to a region of the same length as in the target viral genome. If not completely complementary, the miRNA and its corresponding target viral genome are at least substantially complementary, such that at least six, seven or eight matches are present in the "seed region" near the 5' end of the miR-RNA heteroduplex.

Representative miRNA mimics include, but are not limited to: antisense oligonucleotides, such as the specific antisense oligonucleotides reported in the experimental section below, and the like. Also of interest in certain embodiments are RNAi agents. In representative embodiments, the RNAi agent targets the viral RNA genome. The term "RNAi agent" refers to an agent that modulates expression of viral RNA by a RNA interference mechanism. The RNAi agents employed in one embodiment of the subject invention are small at least partially double-stranded ribonucleic acid molecules, also referred to herein as interfering ribonucleic acids, (e.g., oligoribonucleotides present in duplex structures such as two distinct oligoribonucleotides hybridized to each other or a single ribooligonucleotide that assumes a hairpin formation). By oligoribonucleotide is meant a ribonucleic acid that does not exceed about 100 nt in length, and typically does not exceed about 75 nt length (e.g., no longer than 70 nt, 65 nt, 60 nt, 55 nt, 50 nt, 45 nt, 40 nt, 35 nt, 30 nt, 25 nt, 20 nt or 15 nt). Where the RNA agent is a duplex structure of two distinct ribonucleic acids hybridized to each other, d-siRNA, the length of the duplex structure typically ranges from about 15 to 30 bp, where lengths between about 20 and 25 bps (e.g., 20 bp, 21 bp, 22 bp, 23 bp, 24 by or 25 bp), are of particular interest in certain embodiments. Where the RNA agent is a duplex structure of a single ribonucleic acid that is present in a hairpin formation, a shRNA, the length of the hybridized portion of the hairpin is typically the same as that provided above for the siRNA type of agent or longer by 3 to 9 nucleotides.

miRNA mimics useful for modulating HCV gene expression by RNA interference (RNAi) include short interfering nucleic acid (siNA), short interfering RNA (siRNA), double-stranded RNA (dsRNA), micro-RNA (miRNA), and short hairpin RNA (shRNA) molecules, including cocktails of such small nucleic acid molecules and lipid nanoparticle formulations. In some embodiments, the miRNA mimic is a locked-nucleic-acid-modified oligonucleotide (e.g., LNA-miR and/or LNA-antimiR), which can be formulated in a physiologically acceptable buffer for intravenous injection (0.01 to 10 mg/kg).

In certain embodiments, instead of the RNAi agent being an interfering ribonucleic acid, e.g., a siRNA or shRNA as described above, the RNAi agent may encode an interfering ribonucleic acid. In other words, the RNAi agent may be a transcriptional template of the interfering ribonucleic acid. In these embodiments, the transcriptional template is typically a DNA that encodes the interfering ribonucleic acid. The DNA may be present in a vector, where a variety of different vectors are known in the art (e.g., a plasmid vector, a viral vector, etc.).

As indicated above, the miRNA mimic can be introduced into the target cell(s) using any convenient protocol, where the protocol will vary depending on whether the target cells are in vitro or in vivo. Where the target cells are in vivo, the miRNA agent can be administered to the host using any convenient protocol. In embodiments where the miRNA mimic is a nucleic acid, the protocol employed is typically a nucleic acid administration protocol. The following discussion provides a review of representative nucleic acid administration protocols that may be employed. The nucleic acids may be introduced into tissues or host cells by any number of routes, including viral infection, microinjection, or fusion of vesicles. Jet injection may also be used for intramuscular administration (Furth et al., Anal Biochem 205:365-368, 1992). The nucleic acids may be coated onto gold microparticles, and delivered intradermally by a particle bombardment device, or "gene gun" as described in the literature (Tang et al., Nature 356:152-154, 1992), where gold microprojectiles are coated with the DNA, then bombarded into skin cells. Expression vectors may be used to introduce the nucleic acids into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors such as plasmids or viruses (e.g., retrovirus, lentivirus, adenovirus, and the like), where the vectors are transiently or stably maintained in the transfected cells, usually for a period of at least about one day, more usually for a period of several days to several weeks.

For example, the miRNA mimic can be fed directly to or injected into the host organism containing a target gene (e.g., a target cell infected by a virus). The miRNA may be directly introduced into the cell (e.g., intracellularly), or introduced extracellularly into a cavity, interstitial space, or into the circulation of an organism. Methods for introduction into the oral cavity include direct mixing of RNA with food of the organism. Physical methods of introducing nucleic acids include injection of an RNA solution directly into the cell or extracellular injection into the organism. The agent may be introduced in an amount that allows delivery of at least one copy per cell. Higher doses (e.g., at least 5, 10, 100, 500 or 1000 copies per cell) of the agent may yield more effective inhibition, while lower doses may also be useful.

In certain embodiments, a hydrodynamic nucleic acid administration protocol is employed. Where the agent is a ribonucleic acid, the hydrodynamic ribonucleic acid administration protocol described in detail below is of particular interest. Where the agent is a deoxyribonucleic acid, the hydrodynamic deoxyribonucleic acid administration protocols described in the art are of interest (Chang et al., J Viral, 75:3469-3473, 2001; Liu et al., Gene Ther, 6:1258-1266, 1999; Wolff et al., Science, 247: 1465-1468, 1990; Zhang et al., Hum Gene Ther, 10:1735-1737, 1999; and Zhang et al., Gene Ther, 7:1344-1349, 1999). Additional nucleic acid delivery protocols of interest include, but are not limited to: those described in U.S. Pat. Nos. 5,985,847 and 5,922,687, Acsadi et al., New Biol, 3:71-81, 1991; Hickman et al., Hum Gen Ther, 5:1477-1483, 1994; and Wolff et al., Science, 247: 1465-1468, 1990, etc.

Depending on the nature of the miRNA mimic, the active agent(s) may be administered to the host using any convenient means capable of resulting in the desired reduction of target viral genome amount or load in the infected target cell. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, or intracheal administration. In pharmaceutical dosage forms, the agents may be administered alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill in the art will readily appreciate that dose levels can vary as a function of the specific compound, the nature of the delivery vehicle, and the like. Preferred dosages for a given compound are readily determinable by those of skill in the art by a variety of means. Introduction of an effective amount of a miRNA mimic into a mammalian cell as described above, results in a modulation of target gene(s) expression (e.g., a reduction of target gene(s) expression).

The compositions may be advantageously combined and/or used in combination and/or alternation with other antiviral agents, which are either therapeutic or prophylactic agents, and different from the subject compounds. The compositions may also be advantageously combined and/or used in combination with agents that treat conditions often associated with the viral infections, such as anti-HCV agents. In certain embodiments, administration in conjunction with the subject compositions enhances the efficacy of such agents. Accordingly, the present compounds, when combined or administered in combination with other antiviral agents, can be used in certain embodiments in dosages that are less than the expected amounts when used alone, or less than the calculated amounts for combination therapy.

Exemplary treatment options for hepatitis C (HCV) include interferons (e.g., interferon alfa-2b, interferon alfa-2a, and interferon alfacon-1. Less frequent interferon dosing can be achieved using pegylated interferon (interferon attached to a polyethylene glycol moiety thereby significantly improving its pharmacokinetic profile). Combination therapy with interferon alfa-2b (pegylated and unpegylated) and ribavarin has also been shown to be efficacious for some patient populations. Other agents currently being developed include RNA replication inhibitors (e.g., ViroPharma's VP50406 series), antisense agents, therapeutic vaccines, protease inhibitors, helicase inhibitors and antibody therapy (monoclonal and polyclonal). The compounds and compositions of the present invention may also be used with agents that enhance the body's immune system, including low-dose cyclophosphamide, thymostimulin, vitamins and nutritional supplements (e.g., antioxidants, including vitamins A, C, E, beta-carotene, zinc, selenium, glutathione, coenzyme Q-10 and echinacea), and vaccines.

II. Utility

The subject methods find use in the treatment of a variety of different conditions in which the reduction of a target viral genome amount in a target cell or host comprising the same is desired. In many embodiments, the subject methods find use in the treatment of a host suffering from a viral mediated disease condition. The term "treatment" refers to a therapy designed to bring about a reduction or amelioration of the symptoms associated with the condition afflicting the host.

A variety of hosts are treatable according to the subject methods. Generally such hosts are mammals, animals within the class mammalia, including the orders carnivore (e.g., dogs and cats), rodentia (e.g., mice, guinea pigs, and rats), and primates (e.g., humans, chimpanzees, and monkeys). In some preferred embodiments, the hosts will be humans.

The methods of the present invention may be employed for any viral genome whose abundance in a target cell negatively correlates with a cellular miRNA in that cell. In certain embodiments, the viral genome is a genome of a virus having an RNA genome, where the virus may be from the family Flaviviridae (e.g., a hepacivirus, such as a hepatitis C virus). In certain representative embodiments, the subject invention is employed in methods of treating a host suffering from an HCV mediated disease condition (e.g., associated with infection with non A, non-B hepatitis, NANBH). In these representative embodiments, an effective amount of a miRNA mimic, such as an antisense oligo as exemplified below, is administered to the host such that the amount of HCV genome present in the host cells, particularly liver cells, is reduced.

III. Pharmaceutical Compositions

Also provided are pharmaceutical compositions containing the miRNA mimics compounds employed in the subject methods. Accordingly, the compounds can be formulated for oral or parenteral administration for use in the subject methods.

By way of illustration, the compounds can be admixed with conventional pharmaceutical carriers and excipients (i.e., vehicles) and used in the form of aqueous solutions, tablets, capsules, elixirs, suspensions, syrups, wafers, and the like. Such pharmaceutical compositions contain, in certain embodiments, from about 0.1 to about 90% by weight of the active compound, and more generally from about 1 to about 30% by weight of the active compound. The pharmaceutical compositions may contain common carriers and excipients, such as corn starch or gelatin, lactose, dextrose, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch glycolate and alginic acid.

A liquid composition will generally consist of a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

For example, a powder containing active compound, suspending agent, sucrose and a sweetener can be reconstituted with water to form a suspension. Likewise a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example, polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example, by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example, liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica. Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically acceptable salts that are active when given parenterally can be formulated for intramuscular, intrathecal, or intravenous administration. A typical composition for intramuscular or intrathecal administration will be of a suspension or solution of active ingredient in an oil, for example, arachis oil or sesame oil. A typical composition for intravenous or intrathecal administration will be a sterile isotonic aqueous solution containing, for example, active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol, a chelating agent, for example, ethylenediamine tetraacetic acid, and an anti-oxidant, for example, sodium metabisulphite may be included in the formulation. Alternatively, the solution can be freeze dried and then reconstituted with a suitable solvent just prior to administration.

The compounds of the invention and their pharmaceutically acceptable salts that are active on rectal administration can be formulated as suppositories. A typical suppository formulation will generally consist of active ingredient with a binding and/or lubricating agent such as a gelatin or cocoa butter or other low melting vegetable or synthetic wax or fat.

The compounds of this invention and their pharmaceutically acceptable salts that are active on topical administration can be formulated as transdermal compositions or transdermal delivery devices ("patches"). Such compositions include, for example, a backing, active compound reservoir, a control membrane, liner and contact adhesive. Transdermal patches may be used to provide continuous or discontinuous infusion of the compounds of the present invention in controlled amounts. The construction and use of transdermal patches for the delivery of pharmaceutical agents is well known in the art (See, e.g., U.S. Pat. No. 5,023,252). Such patches may be constructed for continuous, pulsatile, or on demand delivery of pharmaceutical agents.

Optionally, the pharmaceutical composition may contain other pharmaceutically acceptable components, such a buffers, surfactants, antioxidants, viscosity modifying agents, preservatives and the like. Each of these components is well known in the art (See, e.g., U.S. Pat. No. 5,985,310). Other components suitable for use in the formulations of the present invention can be found in Remington's Pharmaceutical Sciences, Mace Publishing Company, Philadelphia, Pa., 17th ed., 1985. In some embodiments, the aqueous cyclodextrin solution further comprises dextrose (e.g., about 5% dextrose).

IV. Kits

Also provided are reagents and kits thereof for practicing one or more of the above-described methods. Typically, the kits at least include a miRNA mimic as described above. The kits may also include a pharmaceutically acceptable delivery vehicle, which may be combined with or separate from the miRNA mimic in the kit (e.g., where the two components may be in the same or separate containers in the kit).

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate (e.g., paper on which the information is printed, in the packaging of the kit, in a package insert, etc.). Yet another means would be a computer readable medium (e.g., diskette, CD, etc.) on which the information has been recorded. Yet another means that may be present is a website address accessible via the internet.

V. Systems

Also provided are systems that find use in practicing the above-described methods. For example, systems for practicing the subject methods may include one or more pharmaceutical formulations, which include the miRNA mimic. The term "system" as employed herein refers to a collection of components, e.g., active agent, delivery vehicle, etc, present in a single composition or as disparate compositions that are brought together for the purpose of practicing the subject methods. For example, separately obtained active agent and delivery vehicle brought together and co-administered to a subject, according to the present invention, are a system according to the present invention.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); C (degrees Centigrade); IFN (interferon); HCV (hepatitis C virus); miR or miRNA (microRNA); MOI (multiplicity of infection); PCR (polymerase chain reaction).

EXAMPLE 1

MicroRNAs for Inhibiting Hepatitis C Virus (HCV) Replication

Materials and Methods

Cell culture. The human hepatoma-derived cell lines Huh7 and their JFH-1 replicon-containing subclone were maintained in DMEM with 10% FCS/10 mM Hepes, penicillin/streptomycin and 2 mM L-glutamine. The JFH-1 full length genomic replicon construct pFGR-JFH-1 was obtained from Dr. Takaji Wakita[20]. A Huh7 cell clone that stably replicates the full length genomic HCV RNA was selected and used in these experiment as described previously[21]. The Huh7.5.1c2 cell line was derived from curing replicon-containing Huh-7.5.1 cells by interferon treatment. Primary murine hepatocytes (Balb C) were collected after collagenase perfusion of the livers for 30 min at 37° C.

miR array analysis. Microarray analysis of total RNA of interferon-stimulated lymphocytes was performed at the Ohio State University Comprehensive Cancer Center Microarray Shared Resource as described[22].

Transfection of miR mimics and anti-miRs into Huh7 or Huh7 replicon cells. When JFH1 replicon containing Huh7 cells (70% confluent) were used for transfection experiments, constant total amounts of miR mimics or anti-miRs (Dharmacon, Lafayette, Colo. and Applied Biosystems, Foster City, Calif., respectively) were combined with Mirus transfection reagent (Mirus Bio/Fisher Scientific) according to the manufacturers instructions and added to the cells (transfection efficiency >90%). Where indicated, IFNβ (DBL Biomedical Laboratories, Piscataway, N.J.) was added to the cultures after 8 hours, and cells were harvested 48 hours post transfection. Viral replication was determined by real-time PCR analysis of viral genomic RNA. Similar, for experiments using infectious HCV, Huh7 cells were transfected with miRs and anti-miRs as described above. HCV infection (MOI=0.05) was performed 8 hours post transfection, and IFNβ was added where indicated to the cultures at the same time. Cells were harvested at the indicated time points during the phase of exponential viral RNA amplification, and viral replication was determined by real-time PCR analysis of viral genomic RNA, or by determination of the number and size of viral foci after 72 hours.

TABLE 1

Mature Murine microRNA Sequences

| miR-# | miR sequence* | SEQ ID |
|---|---|---|
| 1 | UGGAAUGUAAAGAAGUAUGUA | NO: 1 |
| 30c | UGUAAACAUCCUACACUCUCAGC | NO: 2 |
| 122 | UGGAGUGUGACAAUGGUGUUUGU | NO: 3 |
| 125 | UCCCUGAGACCCUAACUUGUGA | NO: 4 |
| 128b | UCACAGUGAACCGGUCUCUUUC | NO: 5 |
| 142 | UGUAGUGUUUCCUACUUUAUGG | NO: 6 |
| 196b | UAGGUAGUUUCCUGUUGUUGG | NO: 7 |
| 296 | AGGGCCCCCCCUCAAUCCUGU | NO: 8 |
| 351 | UCCCUGAGGAGCCCUUUGAGCCUG | NO: 9 |
| 431 | UGUCUUGCAGGCCGUCAUGCAGG | NO: 10 |
| 448 | UUGCAUAUGUAGGAUGUCCCAU | NO: 11 |

*Seed sequences, 5' residues 2-7 of the mature microRNA, are shown in bold.

RNA extraction. Total RNA was isolated using TRIZOL RNA extraction reagent of Invitrogen, according to the manufacturer's instructions.

Real-time PCR. Quantitation of HCV genomic RNA was performed using HCV and β-actin or GAPDH-specific primers as described[15]. Real-time PCR-based quantitation of miRs was performed using miR analysis kits specific for each individual miR (Applied Biosystems) according to the manufacturer's instructions.

Generation of J6CF-JFH1 chimeric HCV genomes. Recombinant PCR was used to replace the J6CF NS5B-3'UTR region in pCV-J6CF (Yanagi et al., Virology, 262:250, 1999) with the corresponding sequences from JFH-1 present in pUC-vJFH (Wakita et al., Nat Med, 11:791, 2005). The NS5B-3'UTR region of JFH-1 and an NS5A-NS5B fragment containing a unique XhoI restriction site from J6CF were amplified using primers: XbaJFH (GATTACGCCAAGCT-TGCATGCCTGCAG, set forth as SEQ ID NO:12), and NS5Bup (CTCCATGTCATACTCCTGGACCGGGGCTC set forth as SEQ ID NO:13); and NS5Blo (GAGCCCCG-GTCCAGGAGTATGACATGGAG set forth as SEQ ID NO:14), and XhoJ6CF (AGGTTCCATCTCTTCCATGC-CCCCCCTCG set forth as SEQ ID NO:15); respectively. The two PCR products were mutually extended and amplified using the primers XhoJ6CF and XbaJFH, and the resultant PCR product was cloned into pGEM-Teasy (Invitrogen, Carlsbad, Calif.) yielding pTe-J6/JFH and the insert was verified by DNA sequencing. Finally, the XhoI to XbaI fragment in pCV-J6CF was replaced by the 2.1 kb XhoI/XbaI fragment excised from pTe-J6/JFH yielding pCVJ6CF/JFHNS5B3'UTR containing the J6CF/JFH1 chimeric HCV genome with the NS5B-3'UTR of J6CF replaced by the corresponding sequences from JFH-1. Infectious JFH-1 and J6CF/JFH1 viruses were produced by transfection of in vitro synthesized genomic HCV RNA into Huh-7.5.1 cells and virus stocks containing 104-105 focus forming units/ml (ffu/ml) were prepared as described (Zhong et al., Proc Natl Acad Sci USA, 102:9294, 2005).

Results and Discussion miRs are a class of small non-coding RNA molecules that function through post-transcriptional regulation of gene expression through a process termed RNA interference (RNAi). Over 500 miR encoding genes, which appear to be exclusively transcribed by RNA polymerase II, have been identified in mammals. These primary microRNAs (pri-miRs) are processed by the enzymes Drosha/DGCR8 into hair-pin loop containing pre-miRs, which are then subject to nuclear export via Exportin 5. Further enzymatic processing of the pre-miRs by Dicer leads to a mature miR duplex that is loaded into the RNA-induced silencing complex (RISC) where the miR guides RISC to complementary mRNAs. Based on the degree of homology between the miR and the mRNA, RISC can inhibit mRNA function by either promoting its cleavage or by inhibiting its translation[3,4]. Particularly the sequence complementarity in the 6- to 8-base-pair "seed region" at the 5' end of the miR-mRNA heteroduplex appears to determine the specificity of miR-targetRNA interactions[5].

RNAi-mediated targeting of viral RNAs was first recognized in plants as part of an antiviral defense mechanism, but it is now apparent that invertebrates also utilize RNAi to combat viral infection[1,6,7]. However, prior to development of the present invention no evidence has been presented in support of a protective RNAi-based antiviral response in mammalian cells. Rather, it has been believed that the potent interferon system has displaced RNAi as the predominant defense against virus infection in mammalian cells[1]. Indeed, several type I interferon (IFNα/β)-regulated gene products such as protein kinase R, the 2'-5' OA synthase/RNAse L system, the adenosine deaminase ADAR1 or the Mx GTPases are important contributors to the antiviral properties of these cytokines[8,9]. However, the possibility that IFNα/β might induce cellular miRs that target viral transcripts and thereby utilize RNAi as part of their arsenal against invading viruses has heretofore been unexplored.

In order to test whether IFNα/β could alter the expression of cellular miRs, microarray technology was used to analyze RNA derived from several cell types stimulated with IFNα/β or IFNγ for various time periods. The initial screening effort identified ~30 miRs whose expression levels were increased or attenuated in response to IFNα/β or IFNγ. Sequence complementarity analysis of these miRs against viral transcripts or viral genomic RNAs was performed with an initial focus on the crucial seed sequence. This approach revealed promising matches among several viruses, most of which harbor an RNA-based genome. Specifically, eight of the IFNβ-induced miRs (miR-1, miR-30, miR-128, miR-196, miR-296, miR-351, miR-431, miR-448) displayed nearly perfect complementarity in their seed sequences with hepatitis C virus (HCV) RNA genomes. This finding was rather intriguing considering that IFNα and IFNβ are the most common treatment regimen for HCV infection[10,11]. A similar analysis of the hepatitis B virus (a DNA virus) yielded no significant matches.

TABLE 2

HCV RNA genome targets of IFNβ-induced Murine Cellular microRNAs

| miR-# | predicted HCV RNA genome target |
|---|---|
| 1 | core, E2, NS3, NS4B, NS5B |
| 30c | core, NS3, NS5 |
| 122 | core, NS2, NS3, NS4B, NS5B |
| 128b | E2, NS3, NS5B |
| 196b | E2, NS4A, NS5B |
| 296 | core, E1, E2, P7, NS2, NS3, NS4B, NS5B |
| 351 | core, NS2, NS3, NS5A, NS5B |
| 431 | E2, NS3, NS4B, NS5B |
| 448 | E1, E2, NS3, NS5A |

HCV is the sole member of the hepacivirus genus of the Flaviviridae family, and is represented by six major genotypes. The virion harbors a 9.6 kb single-stranded RNA genome of positive polarity with highly invariant 5' and 3' untranslated regions[12,13]. After virus entry into the host cell, the viral genome is uncoated and serves as a template for the translation of a single large polyprotein, which is subsequently processed by host and viral proteases. The non-structural viral proteins then initiate the synthesis of a negative-strand RNA, which serves as a replication template for the generation of new positive-strand viral genomes[12,13]. Sequence alignment of the six HCV genotypes illustrated that the putative miR target sites for the IFNβ-induced miRs are located both in areas strictly conserved among all HCV genotypes, as well as in regions that differ between the genotypes such that high seed-sequence complementarity occurs only with selected HCV genotypes.

To verify the microarray studies miR induction in response to IFNβ was analyzed by real-time PCR in the human hepatoma cell line Huh7, and in freshly isolated primary murine hepatocytes. As shown in FIGS. 1a and 1b, IFNβ treatment resulted in a similar level of induction of the prospective antiviral miRs in both cell types as was observed with ISG54, a well characterized IFNα/β-regulated gene[14]. Two miRs (miR-125 and miR-142) that were found IFNβ-unresponsive in the microarray analysis were included as negative controls. Kinetic and dose-response analysis of the induction of miRs by IFNβ was also performed. Time-course analysis revealed that induction of miR-1 and miR-196, which reached peak concentrations within 30 min, occurs very rapidly and thus even precedes the upregulation of ISG54 (FIG. 1c). Similar to ISG54 induction, upregulation of miR-1 and miR-196 followed a classical dose-response curve between 1 and 1,000 U/ml IFNβ (FIG. 1d), and could be blocked by Actinomycin D, indicating that the increased levels of miRs are the result of transcriptional induction.

miR-122 is specifically expressed in the liver, and previous studies using anti-miRs elegantly demonstrated that miR-122 is essential for HCV replication[2]. Whether miR-122 was also subject to regulation by IFNβ was tested. As shown in FIG. 1e, IFNβ-stimulation of Huh7 cells resulted in a transient, but pronounced (~80%) down-modulation of miR-122 levels. Similar to miR induction, 100 U/ml IFNβ induced maximal attenuation of miR-122 expression, and no additional effect was observed with increased IFNβ concentrations (FIG. 1e).

Figure 2:
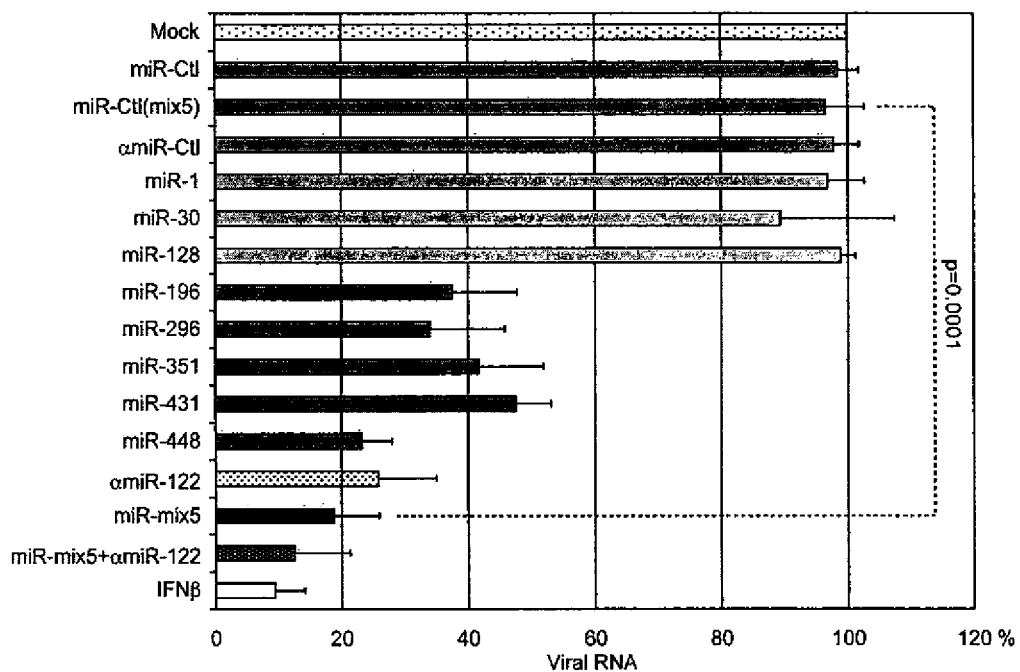
FIGS. 2A-2B show IFNβ-induced miRs display anti-viral activity against HCV. a, JFH1-replicon containing Huh7 cells were transfected with either a single non-specific miR-mimics (miR-Ctl), a pool of control miRs (miR-Ctl(mix5)) or anti-miRs (αmiR-Ctl), or specific miR-mimics corresponding to the eight IFNβ-induced miRs or specific αmiRs as indicated. In addition, a combination of the five miRs that displayed anti-viral activity individually was used (miR-mix5) with or without anti-miR-122 as indicated, and HCV genomic RNA was quantitated by real-time PCR after 48 hrs. b, Same as (a), except Huh7 cells were infected with live JFH-1 virus for 48 hrs (bars represent means+/−std of at least four independent experiments; p-values are derived from paired Student's t-tests).
Figure 2:
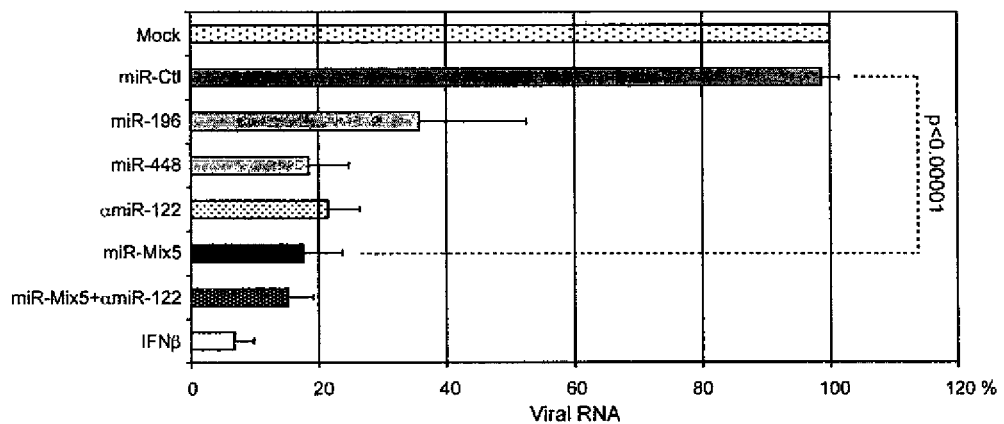

In order to evaluate whether the eight IFNβ-induced miRs with sequence matches in the HCV genome are indeed capable of inhibiting HCV replication, synthetic miR-mimics corresponding to these cellular IFN-induced miRs were transfected into Huh-7 cells, which harbor an autonomously replicating, dicistronic full-length HCV replicon[15,16]. An anti-miR against miR-122 was transfected as a positive control, since it had previously been shown to significantly reduce the abundance of viral replicon RNA in this system[2]. Transfection of either non-specific control miRs (individually or combined) or control anti-miR oligos did not alter the amounts of HCV viral replicon RNA, whereas introduction of anti-miR-122 resulted in an ~70% reduction in viral RNA levels as previously reported (FIG. 2a). Transfection of the eight candidate miRs individually revealed that miRs 196, 296, 351, 431 and 448 were indeed able to substantially attenuate viral replication, whereas introduction of miRs 1, 30 and 128 was without effect in this system (FIG. 2a). Transfection of a mixture of the five functional miR-mimics yielded a >80% reduction in viral RNA load. As IFN induces miRs-196, 296, 351, 431 and 448, but down-regulates miR-122, this cellular response was imitated by transfecting the mix of miR-mimics in combination with the anti-miR-122. Indeed, a small, but reproducible additive inhibitory effect on HCV replication was observed that was similar in efficacy to treatment of the cells with IFNβ (FIG. 2a). Virtually identical results were obtained when Huh7 cells were infected with live JFH1 HCV and either viral genomic RNA levels (FIG. 2b) or viral foci formation was analyzed. In particular, 548 foci were enumerated in Huh7 cell cultures after transfection with negative control miR. In contrast, 240 were enumerated in Huh7 cell cultures after transfection with a mixture of miR-196, 296, 351, 431 and 448, while 121 foci were enumerated in Huh7 cell cultures after transfection with the afore-mentioned miR mixture in combination with anti-miR-122. These results further corroborate the observation made during development of the present invention that the IFNβ-induced alterations in the miR expression profile endow the cells with a pronounced antiviral state.

Figure 3:
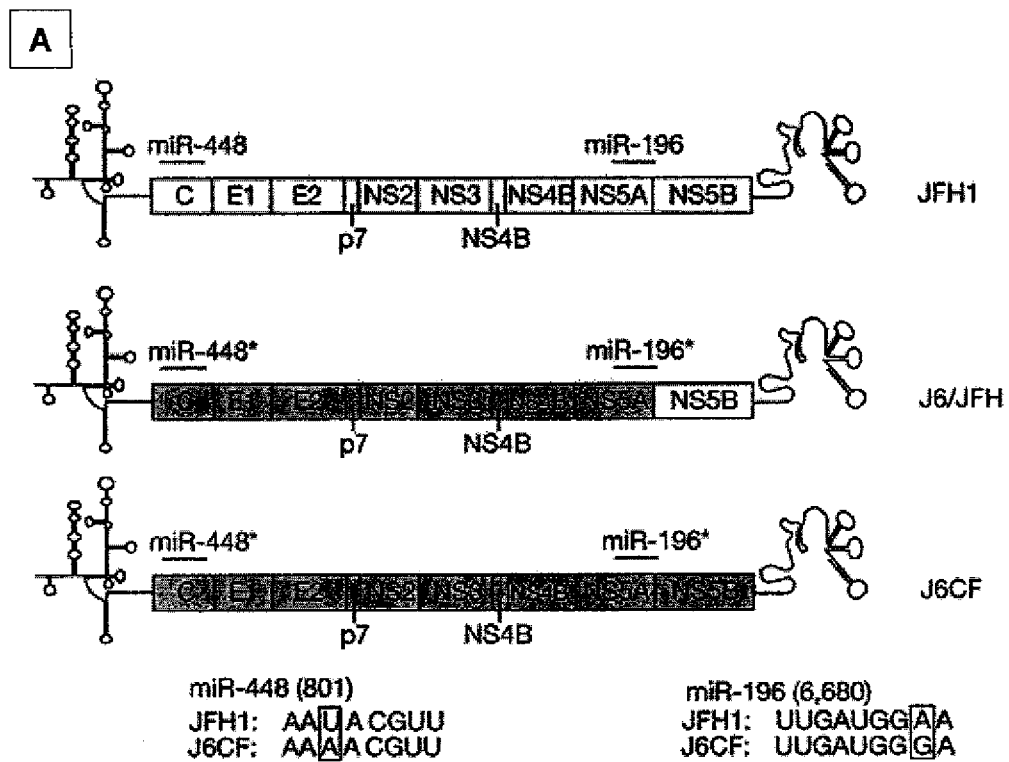
FIG. 3A-3B show IFNβ-induced miRs directly target viral genomic RNA. a and b, An infectious chimeric virus was constructed from JFH1 and J6CF as shown in (a), and described in the supplemental M&M. The Huh7 cell subclone Huh7.5.1c2 were transfected with either miR-196 or miR-448, or with the mutant miR-196* and miR-448* harboring a compensatory mutation in the seed sequence as outlined in (a). Transfected Huh7.5.1c2 cells were infected with JFH1$_{D183}$[23] or chimeric J6/JFH, and HCV genomic RNA was quantitated by real-time PCR after 24 or 60 hrs post infection, respectively, during the phase of exponential viral RNA amplification, to accommodate the difference in replication kinetics between the two viruses (bars represent means+/−sem of at eight independent experiments; p-values are derived from paired Student's t-tests).
Figure 3:
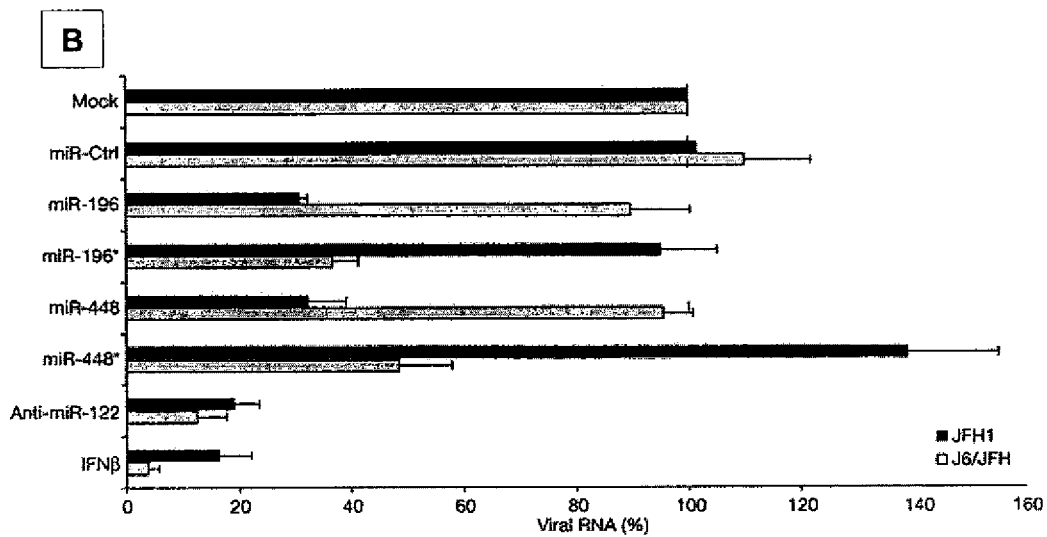

To investigate whether these anti-viral miRs are targeting the HCV genome rather than inducing a non-specific antiviral state through alteration of cellular gene expression, the J6CF HCV molecular clone harboring single nucleotide variations in the predicted target seed sequences for miR-196 and miR-448 as opposed to JFH1 (FIG. 3a) was utilized. As J6CF is non-infectious in-vitro, infection-competent J6CF/JFH1 chimeric viruses that carry the "mutant" miR-448 and miR-196 target sites (Chimera J6/JFH) (FIG. 3a) were employed. miR-196 was effective against JFH1, but not against J6/JFH containing the "mutant" target site. Similarly, miR-448 only inhibited the replication of JFH1 containing the "correct" target site, but was ineffective against J6/JFH (FIG. 3b). Introduction of a compensatory single nucleotide change into miR-196 and miR-448 (designated miR-196* and miR-448*) matching their seed sequence to J6/JFH yielded a reversed efficacy profile compared to the wild-type miRs when they were tested against the chimeric viruses. As such, both miR-196* and miR-448* were unable to subdue replication of JFH1, but clearly inhibited replication of J6/JFH (FIG. 3b). Together, these results indicate that miR-196 and miR-448 are directly targeting the HCV genomic RNA. Thus, IFNβ-induced miRs, in conjunction with the down-regulation of miR-122, induce an antiviral state.

Figure 4:
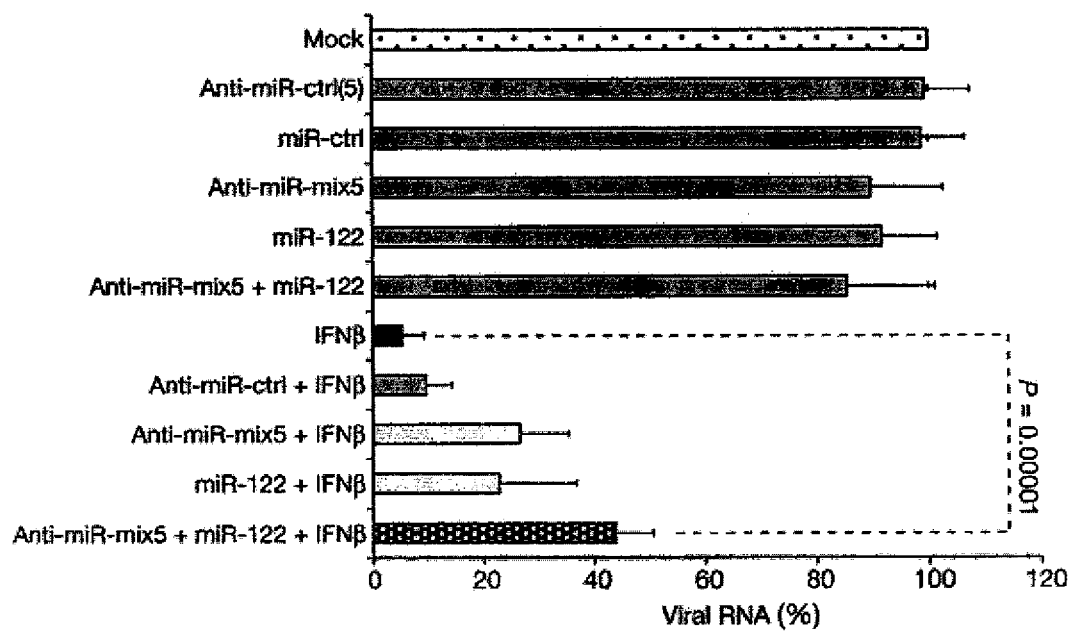
FIG. 4 shows IFNβ-induced miRs mediate anti-viral IFNβ responses of against HCV. JFH1-replicon containing Huh7 were transfected with either non-specific miR-mimics (miR-Ctl), or anti-miRs (αmiR-Ctl), or a pool of anti-miRs (αmiR-Ctl(5)), or a combination of αmiR complementary to the five IFNβ-induced miRs with potent anti-viral effect (αmiR-mix5), and/or with specific miRs and anti-miRs as indicated prior to stimulation with IFNβ for 48 hrs. HCV genomic RNA was quantitated by real-time PCR (bars represent means+/-std of at least four independent experiments; p-values are derived from paired Student's t-tests).

In further experiments, the IFNβ-elicited changes in miR expression were counteracted by transfecting neutralizing anti-miRs against miRs-196, 296, 351, 431 and 448, with and without the inclusion of a miR-122 mimic. IFNβ treatment leads to a >90% reduction in the amount of viral HCV replicon RNA, which is unaffected by transfected non-specific control anti-miRs. As shown in FIG. 4, introduction of the anti-miR mix or of the miR-122 mimic separately attenuated the IFNβ effect to ~75% inhibition. Co-transfection of the anti-miR mix and the miR-122 mimic further reduced the efficacy of IFNβ to ~50%, indicating that modulation of the expression levels of the identified miRs plays an important, albeit not exclusive role in the antiviral effects of IFNβ against HCV.

TABLE 3

Statistical Analysis

| | miR-196 | miR-196* | miR-448 | miR-448* |
|---|---|---|---|---|
| JFH1 | | | | |
| Ctl-miR | 0.00001 | 0.66 | 0.00004 | 0.19 |
| miR-196 | | 0.0014 | | |
| miR-448 | | | | 0.005 |

TABLE 3-continued

Statistical Analysis

| | miR-196 | miR-196* | miR-448 | miR-448* |
|---|---|---|---|---|
| J6/JFH | | | | |
| Ctl-miR | 0.1 | 0.003 | 0.34 | 0.011 |
| miR-196 | | 0.002 | | |
| miR-448 | | | | 0.004 |

Results shown as p-values for a paired T-test.

As determined during development of the present invention, IFNβ up-regulates several cellular miRs, which are capable of inhibiting HCV replication and infection. In addition, down-regulation of miR-122 in response to IFNβ further contributes to the antiviral effects of this cytokine. These findings not only offer a new paradigm for host defense mechanisms that exist in mammalian cells, but also add a new component to the antiviral arsenal employed by interferons. Furthermore, while ample documentation is present in the literature for the developmentally regulated or tissue specific expression of miRs and their dysregulation in malignant cells[17,18], little evidence existed for a direct and immediate transcriptional regulation of miRs by an endogenous ligand such as a cytokine or growth factor. Interestingly, O'Connell et al. reported the IFNβ-induced upregulation of miR-155[19], a miR with no currently identified targets. The delayed induction kinetics observed in their studies supports the model that miR-155 upregulation is mediated by TNFα as part of an autocrine response elicited by IFNβ, rather than by IFNβ itself[19].

References

1. Cullen, *Nat Immunol* 7, 563-7 (2006).
2. Jopling, et al., *Science* 309, 1577-81 (2005).
3. Bartel, *Cell* 116, 281-97 (2004).
4. Ambros, *Nature* 431, 350-5 (2004).
5. Lewis, et al., *Cell* 120, 15-20 (2005).
6. Zamore, *Curr Biol* 14, R198-200 (2004).
7. Baulcombe, *Nature* 431, 356-63 (2004).
8. Katze, et al., *Nat Rev Immunol* 2, 675-87 (2002).
9. Samuel, *Clin Microbiol Rev* 14, 778-809, table of contents (2001).
10. Liang, et al., *Ann Intern Med* 132, 296-305 (2000).
11. Lauer, and Walker, *N Engl J Med* 345, 41-52 (2001).
12. Wieland and Chisari, *J Virol* 79, 9369-80 (2005).
13. Rehermann and Nascimbeni, *Nat Rev Immunol* 5, 215-29 (2005).
14. Larner, et al., *Proc Natl Acad Sci USA* 81, 6733-7 (1984).
15. Zhong, et al., *Proc Natl Acad Sci USA* 102, 9294-9 (2005).
16. Moradpour, et al., *J Virol* 78, 7400-9 (2004).
17. Calin and Croce, *Cancer Res* 66, 7390-4 (2006).
18. Calin and Croce, *Nat Rev Cancer* 6, 857-66 (2006).
19. O'Connell et al., *Proc Natl Acad Sci USA* 104, 1604-9 (2007).
20. Kato, et al., *Gastroenterology* 125, 1808-17 (2003).
21. Cheng, et al., *Proc Natl Acad Sci USA* 103, 8499-504 (2006).
22. Liu, et al., *Proc Natl Acad Sci USA* 101, 9740-4 (2004).
23. Zhong, et al., *J Virol* (22), 11082 (2006)

EXAMPLE 2

MicroRNAs for Reducing Accumulation of Hepatitis C Virus (HCV) RNA In a Subject

This example provides methods for evaluating the microRNA compositions of the present invention in rodent and nonhuman primate models of Hepatitis C virus infection. The methods of the present example are based upon published animal studies of RNAi (See, e.g., WO 2007/076328, and Elmen et al., Nature, 452:896-899, 2008).

Small Animal Models

Evaluating the efficacy of anti-HCV agents in animal models is an important prerequisite to human clinical trials. The best characterized animal system for HCV infection is the chimpanzee. Although clinically relevant, the chimpanzee model suffers from several practical impediments that make use of this model difficult. Due to these factors, several rodent models of chronic hepatitis C infection have been developed. While direct infection, has not yet been possible, stable transfection of either portions or entire HCV genomes into rodents has been accomplished (Yamamoto et al, Hepatology 1995 22(3): 847-855; Galun et al., Journal of Infectious Disease 1995 172(1):25-30; Koike et al., Journal of general Virology 1995 76(12)3031-3038; Pasquinelli et al., Hepatology 1997 25(3): 719-727; Hayashi et al., Princess Takamatsu Symp 1995 25:1430149; Mariya et al., Journal of General Virology 1997 78(7) 1527-1531; Takehara et al., Hepatology 1995 21(3):746-751; Kawamura et al., Hepatology 1997 25(4): 1014-1021). In addition, transplantation of HCV infected human liver into immunocompromised mice results in prolonged detection of HCV RNA in the animal's blood.

A method for expressing hepatitis C virus in an in vivo animal model has been developed (Vierling, International PCT Publication No. WO 99/16307). Briefly viable, HCV infected human hepatocytes are transplanted into a liver parenchyma of a scid/scid mouse host. The scid/scid mouse host is then maintained in a viable state, whereby viable, morphologically intact human hepatocytes persist in the donor tissue and hepatitis C virus is replicated in the persisting human hepatocytes. This model provides an effective means for the study of HCV inhibition by microRNA administration in vivo.

Nonhuman Primate Models

GBV-B is very closely related to human hepatitis C virus and causes hepatitis in tamarins and marmosets. Thus, GBV-B infection of tamarins and marmosets are suitable nonhuman primate models for testing antiviral compounds and vaccines for HCV infection. The GBV-B model is an appropriate system to test whether the microRNA-based therapies of the present invention are likely to work on humans chronically infected with HCV. In an initial study, two animals are inoculated with GBV-B and treatment with the microRNA compositions of the present invention is initiated one day post infection. Another two animals are inoculated with GBV-B and are untreated to serve as negative controls. The animals are monitored to determine the effect of the therapy of GBV-B infection. Blood draws are performed over the course of the study to determine viral titers. Dosing of microRNA compositions in the treated animals is repeated at days 1, 3, and 7 after inoculation at day 0. The treated animals are contemplated to have a measurable inhibition of GBV-B over a 1-4 week time course as compared to the untreated control animals. In addition, several animals with established GBV infections as treated with the microRNA compositions of the present invention at days 28, 31, and 35 post-infection. These animals are contemplated to show a measurable following dosing, as compared to historic untreated controls.

In a further the microRNA compositions of the present invention are evaluated in HCV-infected chimpanzees. The compositions are administered by IV. The chimpanzees to be used are selected from a group of HCV chronic animals. The study is conducted in two phases: pharmacokinetics and efficacy. The pharmacokinetics portion of the study is conducted in two non-HCV-infected animals. Blood samples are obtained at times: 0 min, 15 min, 30 min, 24 hr, and days 3, 7 and 14. Liver biopsies are obtained at 24 hr and 14 days. The efficacy involves testing of the antiviral compound in 2 or more HCV infected chimpanzees.

Animals receive 4 weekly IV injections with the antiviral microRNA formulations. Blood samples are obtained at −4, −2, and 0 weeks, then weekly for 6 weeks, and then every other week for 4 additional weeks. Liver biopsies are obtained at −4 weeks and +4 weeks (one week after last injection). The animals are monitored for blood chemistries and complete blood counts (CBC) at all bleeds. At the sign of any serious adverse effects, treatment is stopped. For each animal, multiple blood samples are taken to monitor the viral RNA levels in the serum. Liver needle biopsies are requested at two time points for analysis of viral RNA load in the liver, level of microRNA targeted to liver, and changes in liver gene expression. Viral RNA is monitored by real time quantitative RT-PCR.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in the relevant fields, are intended to be within the scope of the following claims.

I claim:

1. A method for reducing accumulation of Hepatitis C virus RNA, comprising:

introducing a first isolated nucleic acid molecule into a Hepatitis C virus (HCV)-infected target cell in an amount sufficient for reducing accumulation of HCV RNA in said target cell, wherein said first isolated nucleic acid molecule is a miRNA mimic comprising the nucleotide sequence of a cellular microRNA selected from the group consisting of miR-196, miR-296, miR-351, miR-431 and miR-448.

2. The method of claim 1, wherein said cellular microRNA is said miR-196 consisting of the nucleotide sequence set forth as SEQ ID NO:7.

3. The method of claim 1, wherein said cellular microRNA is said miR-296 consisting of the nucleotide sequence set forth as SEQ ID NO:8.

4. The method of claim 1, wherein said cellular microRNA is said miR-351 consisting of the nucleotide sequence set forth as SEQ ID NO:9.

5. The method of claim 1, wherein said cellular microRNA is said miR-431 consisting of the nucleotide sequence set forth as SEQ ID NO:10.

6. The method of claim 1, wherein said cellular microRNA is said miR-448 consisting of the nucleotide sequence set forth as SEQ ID NO:11.

7. The method of claim 1, further comprising introducing a second isolated nucleic acid molecule into said HCV-infected target cell, wherein said second isolated nucleic acid molecule is an anti-miRNA comprising the nucleotide sequence complementary to miR-122.

8. The method of claim 7, wherein said miR-122 consists of the nucleotide sequence set forth as SEQ ID NO:3.

9. The method of claim 1, wherein said target cell is in vitro.

10. The method of claim 1, wherein said target cell is in vivo.

11. The method of claim 10, wherein said method comprises administering the first isolated nucleic acid molecule to a subject comprising said HCV-infected target cell.

12. The method of claim 1, wherein said miRNA mimic is a mature miRNA.

* * * * *

SEQUENCE LISTING

```
<160> NUMBER OF SEQ ID NOS: 125

<210> SEQ ID NO 1
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1
uggaauguaa agaaguaugu a                                                 21

<210> SEQ ID NO 2
<211> LENGTH: 23
<212> TYPE: RNA
<213> ORGANISM: Artificial Sequence
<220> FEATURE:
<223> OTHER INFORMATION: Synthetic Construct

<400> SEQUENCE: 2
uguaaacauc cuacacucuc agc                                               23

<210> SEQ ID NO 3
<211> LENGTH: 23
<212> TYPE: RNA
<213> ORGANISM: Artificial Sequence
<220> FEATURE:
<223> OTHER INFORMATION: Synthetic Construct

<400> SEQUENCE: 3
uggaguguga caaugguguu ugu                                               23

<210> SEQ ID NO 4
<211> LENGTH: 22
<212> TYPE: RNA
<213> ORGANISM: Artificial Sequence
<220> FEATURE:
<223> OTHER INFORMATION: Synthetic Construct

<400> SEQUENCE: 4
ucccugagac ccuaacuugu ga                                                22

<210> SEQ ID NO 5
<211> LENGTH: 22
<212> TYPE: RNA
<213> ORGANISM: Artificial Sequence
<220> FEATURE:
<223> OTHER INFORMATION: Synthetic Construct
```

-continued

```
<400> SEQUENCE: 5
ucacagugaa ccggucucuu uc                                          22

<210> SEQ ID NO 6
<211> LENGTH: 22
<212> TYPE: RNA
<213> ORGANISM: Artificial Sequence
<220> FEATURE:
<223> OTHER INFORMATION: Synthetic Construct

<400> SEQUENCE: 6
uguaguguuu ccuacuuuau gg                                          22

<210> SEQ ID NO 7
<211> LENGTH: 21
<212> TYPE: RNA
<213> ORGANISM: Artificial Sequence
<220> FEATURE:
<223> OTHER INFORMATION: Synthetic Construct

<400> SEQUENCE: 7
uagguaguuu ccuguuguug g                                           21

<210> SEQ ID NO 8
<211> LENGTH: 21
<212> TYPE: RNA
<213> ORGANISM: Artificial Sequence
<220> FEATURE:
<223> OTHER INFORMATION: Synthetic Construct

<400> SEQUENCE: 8 agggccccccc cucaauccug u                                          21

<210> SEQ ID NO 9
<211> LENGTH: 24
<212> TYPE: RNA
<213> ORGANISM: Artificial Sequence
<220> FEATURE:
<223> OTHER INFORMATION: Synthetic Construct

<400> SEQUENCE: 9
ucccugagga gcccuuugag ccug                                        24

<210> SEQ ID NO 10
<211> LENGTH: 23
<212> TYPE: RNA
<213> ORGANISM: Artificial Sequence
<220> FEATURE:
<223> OTHER INFORMATION: Synthetic Construct

<400> SEQUENCE: 10
ugucuugcag gccgucaugc agg                                         23

<210> SEQ ID NO 11
<211> LENGTH: 22
<212> TYPE: RNA
<213> ORGANISM: Artificial Sequence
<220> FEATURE:
<223> OTHER INFORMATION: Synthetic Construct

<400> SEQUENCE: 11
uugcauaugu aggauguccc au                                          22

<210> SEQ ID NO 12
<211> LENGTH: 26
<212> TYPE: DNA
```

```
<213> ORGANISM: Artificial Sequence
<220> FEATURE:
<223> OTHER INFORMATION: Synthetic Construct

<400> SEQUENCE: 12
gattacgcca agcttgcatg cctgca                                        26

<210> SEQ ID NO 13
<211> LENGTH: 29
<212> TYPE: DNA
<213> ORGANISM: Artificial Sequence
<220> FEATURE:
<223> OTHER INFORMATION: Synthetic Construct

<400> SEQUENCE: 13
ctccatgtca tactcctgga ccggggctc                                     29

<210> SEQ ID NO 14
<211> LENGTH: 29
<212> TYPE: DNA
<213> ORGANISM: Artificial Sequence
<220> FEATURE:
<223> OTHER INFORMATION: Synthetic Construct

<400> SEQUENCE: 14
gagccccggt ccaggagtat gacatggag                                     29

<210> SEQ ID NO 15
<211> LENGTH: 29
<212> TYPE: DNA
<213> ORGANISM: Artificial Sequence
<220> FEATURE:
<223> OTHER INFORMATION: Synthetic Construct

<400> SEQUENCE: 15
aggttccatc tcttccatgc cccccctcg                                     29

<210> SEQ ID NO 16
<211> LENGTH: 23
<212> TYPE: RNA
<213> ORGANISM: Artificial Sequence
<220> FEATURE:
<223> OTHER INFORMATION: Synthetic Construct

<400> SEQUENCE: 16
auacauacac gcacacauaa gac                                           23

<210> SEQ ID NO 17
<211> LENGTH: 22
<212> TYPE: RNA
<213> ORGANISM: Artificial Sequence
<220> FEATURE:
<223> OTHER INFORMATION: Synthetic Construct

<400> SEQUENCE: 17
uaaggugcau cuagugcaga ua                                            22

<210> SEQ ID NO 18
<211> LENGTH: 21
<212> TYPE: RNA
<213> ORGANISM: Artificial Sequence
<220> FEATURE:
<223> OTHER INFORMATION: Synthetic Construct

<400> SEQUENCE: 18
auguaugugu gcaugugcau g                                             21
```

```
<210> SEQ ID NO 19
<211> LENGTH: 21
<212> TYPE: RNA
<213> ORGANISM: Artificial Sequence
<220> FEATURE:
<223> OTHER INFORMATION: Synthetic Construct

<400> SEQUENCE: 19
uucaaguaau ccaggauagg c                                             21

<210> SEQ ID NO 20
<211> LENGTH: 23
<212> TYPE: RNA
<213> ORGANISM: Artificial Sequence
<220> FEATURE:
<223> OTHER INFORMATION: Synthetic Construct

<400> SEQUENCE: 20
auacauacac gcacacauaa gac                                           23

<210> SEQ ID NO 21
<211> LENGTH: 22
<212> TYPE: RNA
<213> ORGANISM: Artificial Sequence
<220> FEATURE:
<223> OTHER INFORMATION: Synthetic Construct

<400> SEQUENCE: 21
uggcagugua uuguuagcug gu                                            22

<210> SEQ ID NO 22
<211> LENGTH: 22
<212> TYPE: RNA
<213> ORGANISM: Artificial Sequence
<220> FEATURE:
<223> OTHER INFORMATION: Synthetic Construct

<400> SEQUENCE: 22
uugguccccu ucaaccagcu gu                                            22

<210> SEQ ID NO 23
<211> LENGTH: 23
<212> TYPE: RNA
<213> ORGANISM: Artificial Sequence
<220> FEATURE:
<223> OTHER INFORMATION: Synthetic Construct

<400> SEQUENCE: 23
acuccauuug uuuugaugau gga                                           23

<210> SEQ ID NO 24
<211> LENGTH: 23
<212> TYPE: RNA
<213> ORGANISM: Artificial Sequence
<220> FEATURE:
<223> OTHER INFORMATION: Synthetic Construct

<400> SEQUENCE: 24
aaagugcuac uacuuuugag ucu                                           23

<210> SEQ ID NO 25
<211> LENGTH: 23
<212> TYPE: RNA
<213> ORGANISM: Artificial Sequence
<220> FEATURE:
<223> OTHER INFORMATION: Synthetic Construct
```

```
<400> SEQUENCE: 25
uuuggcacua gcacauuuuu gcu                                          23

<210> SEQ ID NO 26
<211> LENGTH: 21
<212> TYPE: RNA
<213> ORGANISM: Artificial Sequence
<220> FEATURE:
<223> OTHER INFORMATION: Synthetic Construct

<400> SEQUENCE: 26
ucguaccgug aguaauaaug c                                            21

<210> SEQ ID NO 27
<211> LENGTH: 21
<212> TYPE: RNA
<213> ORGANISM: Artificial Sequence
<220> FEATURE:
<223> OTHER INFORMATION: Synthetic Construct

<400> SEQUENCE: 27
cauuauuacu uuugguacgc g                                            21

<210> SEQ ID NO 28
<211> LENGTH: 22
<212> TYPE: RNA
<213> ORGANISM: Artificial Sequence
<220> FEATURE:
<223> OTHER INFORMATION: Synthetic Construct

<400> SEQUENCE: 28
uaugcaaggg caagcucucu uc                                           22

<210> SEQ ID NO 29
<211> LENGTH: 22
<212> TYPE: RNA
<213> ORGANISM: Artificial Sequence
<220> FEATURE:
<223> OTHER INFORMATION: Synthetic Construct

<400> SEQUENCE: 29
auauacauac acacaccuac ac                                           22

<210> SEQ ID NO 30
<211> LENGTH: 22
<212> TYPE: RNA
<213> ORGANISM: Artificial Sequence
<220> FEATURE:
<223> OTHER INFORMATION: Synthetic Construct

<400> SEQUENCE: 30
auauacauac acacaccaac ac                                           22

<210> SEQ ID NO 31
<211> LENGTH: 21
<212> TYPE: RNA
<213> ORGANISM: Artificial Sequence
<220> FEATURE:
<223> OTHER INFORMATION: Synthetic Construct

<400> SEQUENCE: 31
uagcaccauc ugaaaucggu u                                            21

<210> SEQ ID NO 32
<211> LENGTH: 22
<212> TYPE: RNA
```

```
<213> ORGANISM: Artificial Sequence
<220> FEATURE:
<223> OTHER INFORMATION: Synthetic Construct

<400> SEQUENCE: 32
aacauucauu gcugucggug gg                                              22

<210> SEQ ID NO 33
<211> LENGTH: 23
<212> TYPE: RNA
<213> ORGANISM: Artificial Sequence
<220> FEATURE:
<223> OTHER INFORMATION: Synthetic Construct

<400> SEQUENCE: 33
uaggcagugu aauuagcuga uug                                             23

<210> SEQ ID NO 34
<211> LENGTH: 23
<212> TYPE: RNA
<213> ORGANISM: Artificial Sequence
<220> FEATURE:
<223> OTHER INFORMATION: Synthetic Construct

<400> SEQUENCE: 34
aaagugcuac uacuuuugag ucu                                             23

<210> SEQ ID NO 35
<211> LENGTH: 21
<212> TYPE: RNA
<213> ORGANISM: Artificial Sequence
<220> FEATURE:
<223> OTHER INFORMATION: Synthetic Construct

<400> SEQUENCE: 35
uggaagacuu gugauuuugu u                                               21

<210> SEQ ID NO 36
<211> LENGTH: 23
<212> TYPE: RNA
<213> ORGANISM: Artificial Sequence
<220> FEATURE:
<223> OTHER INFORMATION: Synthetic Construct

<400> SEQUENCE: 36
gaauguugcu cggugaaccc cuu                                             23

<210> SEQ ID NO 37
<211> LENGTH: 23
<212> TYPE: RNA
<213> ORGANISM: Artificial Sequence
<220> FEATURE:
<223> OTHER INFORMATION: Synthetic Construct

<400> SEQUENCE: 37 uaagcacua gugguuccgu uua                                              23

<210> SEQ ID NO 38
<211> LENGTH: 24
<212> TYPE: RNA
<213> ORGANISM: Artificial Sequence
<220> FEATURE:
<223> OTHER INFORMATION: Synthetic Construct

<400> SEQUENCE: 38
ucucacacag aaaucgcacc cguc                                            24
```

```
<210> SEQ ID NO 39
<211> LENGTH: 21
<212> TYPE: RNA
<213> ORGANISM: Artificial Sequence
<220> FEATURE:
<223> OTHER INFORMATION: Synthetic Construct

<400> SEQUENCE: 39
uucaaguaau ccaggauagg c                                              21

<210> SEQ ID NO 40
<211> LENGTH: 21
<212> TYPE: RNA
<213> ORGANISM: Artificial Sequence
<220> FEATURE:
<223> OTHER INFORMATION: Synthetic Construct

<400> SEQUENCE: 40
ucgaucgguc ggucggucag u                                              21

<210> SEQ ID NO 41
<211> LENGTH: 19
<212> TYPE: RNA
<213> ORGANISM: Artificial Sequence
<220> FEATURE:
<223> OTHER INFORMATION: Synthetic Construct

<400> SEQUENCE: 41
gugcauugua guugcauug                                                 19

<210> SEQ ID NO 42
<211> LENGTH: 22
<212> TYPE: RNA
<213> ORGANISM: Artificial Sequence
<220> FEATURE:
<223> OTHER INFORMATION: Synthetic Construct

<400> SEQUENCE: 42
ugguuuaccg ucccacauac au                                             22

<210> SEQ ID NO 43
<211> LENGTH: 23
<212> TYPE: RNA
<213> ORGANISM: Artificial Sequence
<220> FEATURE:
<223> OTHER INFORMATION: Synthetic Construct

<400> SEQUENCE: 43
uaagugcuuc cauguuuugg uga                                            23

<210> SEQ ID NO 44
<211> LENGTH: 23
<212> TYPE: RNA
<213> ORGANISM: Artificial Sequence
<220> FEATURE:
<223> OTHER INFORMATION: Synthetic Construct

<400> SEQUENCE: 44
uauggcuuuu uauuccuaug uga                                            23

<210> SEQ ID NO 45
<211> LENGTH: 22
<212> TYPE: RNA
<213> ORGANISM: Artificial Sequence
<220> FEATURE:
<223> OTHER INFORMATION: Synthetic Construct
```

```
<400> SEQUENCE: 45
uuuguucguu cggcucgcgu ga                                              22

<210> SEQ ID NO 46
<211> LENGTH: 20
<212> TYPE: RNA
<213> ORGANISM: Artificial Sequence
<220> FEATURE:
<223> OTHER INFORMATION: Synthetic Construct

<400> SEQUENCE: 46
uaaggcacgc ggugaaugcc                                                 20

<210> SEQ ID NO 47
<211> LENGTH: 23
<212> TYPE: RNA
<213> ORGANISM: Artificial Sequence
<220> FEATURE:
<223> OTHER INFORMATION: Synthetic Construct

<400> SEQUENCE: 47
uauggcuuuu uauuccuaug uga                                             23

<210> SEQ ID NO 48
<211> LENGTH: 23
<212> TYPE: RNA
<213> ORGANISM: Artificial Sequence
<220> FEATURE:
<223> OTHER INFORMATION: Synthetic Construct

<400> SEQUENCE: 48
caaagaauuc uccuuuggg cuu                                              23

<210> SEQ ID NO 49
<211> LENGTH: 23
<212> TYPE: RNA
<213> ORGANISM: Artificial Sequence
<220> FEATURE:
<223> OTHER INFORMATION: Synthetic Construct

<400> SEQUENCE: 49
cccaguguuu agacuaccug uuc                                             23

<210> SEQ ID NO 50
<211> LENGTH: 22
<212> TYPE: RNA
<213> ORGANISM: Artificial Sequence
<220> FEATURE:
<223> OTHER INFORMATION: Synthetic Construct

<400> SEQUENCE: 50
aauauaacac agauggccug uu                                              22

<210> SEQ ID NO 51
<211> LENGTH: 22
<212> TYPE: RNA
<213> ORGANISM: Artificial Sequence
<220> FEATURE:
<223> OTHER INFORMATION: Synthetic Construct

<400> SEQUENCE: 51
ucacagugaa ccggucucuu uu                                              22

<210> SEQ ID NO 52
<211> LENGTH: 22
<212> TYPE: RNA
```

```
<213> ORGANISM: Artificial Sequence
<220> FEATURE:
<223> OTHER INFORMATION: Synthetic Construct

<400> SEQUENCE: 52
ucagugcacu acagaacuuu gu                                              22

<210> SEQ ID NO 53
<211> LENGTH: 22
<212> TYPE: RNA
<213> ORGANISM: Artificial Sequence
<220> FEATURE:
<223> OTHER INFORMATION: Synthetic Construct

<400> SEQUENCE: 53
aucauagagg aacauccacu uu                                              22

<210> SEQ ID NO 54
<211> LENGTH: 23
<212> TYPE: RNA
<213> ORGANISM: Artificial Sequence
<220> FEATURE:
<223> OTHER INFORMATION: Synthetic Construct

<400> SEQUENCE: 54
acuucaccug guccacuagc cgu                                             23

<210> SEQ ID NO 55
<211> LENGTH: 21
<212> TYPE: RNA
<213> ORGANISM: Artificial Sequence
<220> FEATURE:
<223> OTHER INFORMATION: Synthetic Construct

<400> SEQUENCE: 55
uagguaguuu cauguuguug g                                               21

<210> SEQ ID NO 56
<211> LENGTH: 21
<212> TYPE: RNA
<213> ORGANISM: Artificial Sequence
<220> FEATURE:
<223> OTHER INFORMATION: Synthetic Construct

<400> SEQUENCE: 56
ugauugucca aacgcaauuc u                                               21

<210> SEQ ID NO 57
<211> LENGTH: 23
<212> TYPE: RNA
<213> ORGANISM: Artificial Sequence
<220> FEATURE:
<223> OTHER INFORMATION: Synthetic Construct

<400> SEQUENCE: 57
uucagcuccu auaugaugcc uuu                                             23

<210> SEQ ID NO 58
<211> LENGTH: 21
<212> TYPE: RNA
<213> ORGANISM: Artificial Sequence
<220> FEATURE:
<223> OTHER INFORMATION: Synthetic Construct

<400> SEQUENCE: 58
ugcugacccc uaguccagug c                                               21
```

<210> SEQ ID NO 59
<211> LENGTH: 22
<212> TYPE: RNA
<213> ORGANISM: Artificial Sequence
<220> FEATURE:
<223> OTHER INFORMATION: Synthetic Construct

<400> SEQUENCE: 59
aaaccguuac cauuacugag uu                                             22

<210> SEQ ID NO 60
<211> LENGTH: 21
<212> TYPE: RNA
<213> ORGANISM: Artificial Sequence
<220> FEATURE:
<223> OTHER INFORMATION: Synthetic Construct

<400> SEQUENCE: 60
aucgggaaug ucguguccgc c                                              21

<210> SEQ ID NO 61
<211> LENGTH: 22
<212> TYPE: RNA
<213> ORGANISM: Artificial Sequence
<220> FEATURE:
<223> OTHER INFORMATION: Synthetic Construct

<400> SEQUENCE: 61
aggcaagaug cuggcauagc ug                                             22

<210> SEQ ID NO 62
<211> LENGTH: 22
<212> TYPE: RNA
<213> ORGANISM: Artificial Sequence
<220> FEATURE:
<223> OTHER INFORMATION: Synthetic Construct

<400> SEQUENCE: 62
agaucagaag gugacugugg cu                                             22

<210> SEQ ID NO 63
<211> LENGTH: 17
<212> TYPE: RNA
<213> ORGANISM: Artificial Sequence
<220> FEATURE:
<223> OTHER INFORMATION: Synthetic Construct

<400> SEQUENCE: 63
agcugguguu gugaauc                                                   17

<210> SEQ ID NO 64
<211> LENGTH: 22
<212> TYPE: RNA
<213> ORGANISM: Artificial Sequence
<220> FEATURE:
<223> OTHER INFORMATION: Synthetic Construct

<400> SEQUENCE: 64
ucagugcauc acagaacuuu gu                                             22

<210> SEQ ID NO 65
<211> LENGTH: 23
<212> TYPE: RNA
<213> ORGANISM: Artificial Sequence
<220> FEATURE:
<223> OTHER INFORMATION: Synthetic Construct

```
<400> SEQUENCE: 65
ucaagagcaa uaacgaaaaa ugu                                            23

<210> SEQ ID NO 66
<211> LENGTH: 22
<212> TYPE: RNA
<213> ORGANISM: Artificial Sequence
<220> FEATURE:
<223> OTHER INFORMATION: Synthetic Construct

<400> SEQUENCE: 66
aagcccuuac cccaaaaagc au                                             22

<210> SEQ ID NO 67
<211> LENGTH: 22
<212> TYPE: RNA
<213> ORGANISM: Artificial Sequence
<220> FEATURE:
<223> OTHER INFORMATION: Synthetic Construct

<400> SEQUENCE: 67
cuuuuugcgg ucugggcuug cu                                             22

<210> SEQ ID NO 68
<211> LENGTH: 23
<212> TYPE: RNA
<213> ORGANISM: Artificial Sequence
<220> FEATURE:
<223> OTHER INFORMATION: Synthetic Construct

<400> SEQUENCE: 68
uagcaccauu ugaaaucagu guu                                            23

<210> SEQ ID NO 69
<211> LENGTH: 23
<212> TYPE: RNA
<213> ORGANISM: Artificial Sequence
<220> FEATURE:
<223> OTHER INFORMATION: Synthetic Construct

<400> SEQUENCE: 69
uccgucucag uuacuuuaua gcc                                            23

<210> SEQ ID NO 70
<211> LENGTH: 21
<212> TYPE: RNA
<213> ORGANISM: Artificial Sequence
<220> FEATURE:
<223> OTHER INFORMATION: Synthetic Construct

<400> SEQUENCE: 70
uagcaccauc ugaaaucggu u                                              21

<210> SEQ ID NO 71
<211> LENGTH: 20
<212> TYPE: RNA
<213> ORGANISM: Artificial Sequence
<220> FEATURE:
<223> OTHER INFORMATION: Synthetic Construct

<400> SEQUENCE: 71
uaaggcacgc ggugaaugcc                                                20

<210> SEQ ID NO 72
<211> LENGTH: 22
<212> TYPE: RNA
```

```
<213> ORGANISM: Artificial Sequence
<220> FEATURE:
<223> OTHER INFORMATION: Synthetic Construct

<400> SEQUENCE: 72
uagcuuauca gacugauguu ga                                              22

<210> SEQ ID NO 73
<211> LENGTH: 20
<212> TYPE: RNA
<213> ORGANISM: Artificial Sequence
<220> FEATURE:
<223> OTHER INFORMATION: Synthetic Construct

<400> SEQUENCE: 73
uagcaccauu ugaaaucggu                                                 20

<210> SEQ ID NO 74
<211> LENGTH: 22
<212> TYPE: RNA
<213> ORGANISM: Artificial Sequence
<220> FEATURE:
<223> OTHER INFORMATION: Synthetic Construct

<400> SEQUENCE: 74
ugagguagua aguuguauug uu                                              22

<210> SEQ ID NO 75
<211> LENGTH: 22
<212> TYPE: RNA
<213> ORGANISM: Artificial Sequence
<220> FEATURE:
<223> OTHER INFORMATION: Synthetic Construct

<400> SEQUENCE: 75
aacauucauu gcugucggug gg                                              22

<210> SEQ ID NO 76
<211> LENGTH: 22
<212> TYPE: RNA
<213> ORGANISM: Artificial Sequence
<220> FEATURE:
<223> OTHER INFORMATION: Synthetic Construct

<400> SEQUENCE: 76
aucacacaaa ggcaacuuuu gu                                              22

<210> SEQ ID NO 77
<211> LENGTH: 23
<212> TYPE: RNA
<213> ORGANISM: Artificial Sequence
<220> FEATURE:
<223> OTHER INFORMATION: Synthetic Construct

<400> SEQUENCE: 77
ugugcaaauc uaugcaaaac uga                                             23

<210> SEQ ID NO 78
<211> LENGTH: 23
<212> TYPE: RNA
<213> ORGANISM: Artificial Sequence
<220> FEATURE:
<223> OTHER INFORMATION: Synthetic Construct

<400> SEQUENCE: 78
ccuaguaggu gcucaguaag ugu                                             23
```

```
<210> SEQ ID NO 79
<211> LENGTH: 22
<212> TYPE: RNA
<213> ORGANISM: Artificial Sequence
<220> FEATURE:
<223> OTHER INFORMATION: Synthetic Construct

<400> SEQUENCE: 79
aggcaagaug cuggcauagc ug                                              22

<210> SEQ ID NO 80
<211> LENGTH: 22
<212> TYPE: RNA
<213> ORGANISM: Artificial Sequence
<220> FEATURE:
<223> OTHER INFORMATION: Synthetic Construct

<400> SEQUENCE: 80
uauacaaggg caagcucucu gu                                              22

<210> SEQ ID NO 81
<211> LENGTH: 21
<212> TYPE: RNA
<213> ORGANISM: Artificial Sequence
<220> FEATURE:
<223> OTHER INFORMATION: Synthetic Construct

<400> SEQUENCE: 81
aucgggaaug ucguguccgc c                                               21

<210> SEQ ID NO 82
<211> LENGTH: 22
<212> TYPE: RNA
<213> ORGANISM: Artificial Sequence
<220> FEATURE:
<223> OTHER INFORMATION: Synthetic Construct

<400> SEQUENCE: 82
ugguuuaccg ucccacauac au                                              22

<210> SEQ ID NO 83
<211> LENGTH: 22
<212> TYPE: RNA
<213> ORGANISM: Artificial Sequence
<220> FEATURE:
<223> OTHER INFORMATION: Synthetic Construct

<400> SEQUENCE: 83
aaggagcuca cagucuauug ag                                              22

<210> SEQ ID NO 84
<211> LENGTH: 23
<212> TYPE: RNA
<213> ORGANISM: Artificial Sequence
<220> FEATURE:
<223> OTHER INFORMATION: Synthetic Construct

<400> SEQUENCE: 84
uaaagugcuu auagugcagg uag                                             23

<210> SEQ ID NO 85
<211> LENGTH: 22
<212> TYPE: RNA
<213> ORGANISM: Artificial Sequence
<220> FEATURE:
<223> OTHER INFORMATION: Synthetic Construct
```

```
<400> SEQUENCE: 85
caaagugcuc auagugcagg ua                                        22

<210> SEQ ID NO 86
<211> LENGTH: 21
<212> TYPE: RNA
<213> ORGANISM: Artificial Sequence
<220> FEATURE:
<223> OTHER INFORMATION: Synthetic Construct

<400> SEQUENCE: 86
uucaaguaau ccaggauagg c                                         21

<210> SEQ ID NO 87
<211> LENGTH: 21
<212> TYPE: RNA
<213> ORGANISM: Artificial Sequence
<220> FEATURE:
<223> OTHER INFORMATION: Synthetic Construct

<400> SEQUENCE: 87
cauuauuacu uuugguacgc g                                         21

<210> SEQ ID NO 88
<211> LENGTH: 21
<212> TYPE: RNA
<213> ORGANISM: Artificial Sequence
<220> FEATURE:
<223> OTHER INFORMATION: Synthetic Construct

<400> SEQUENCE: 88
ucguaccgug aguaauaaug c                                         21

<210> SEQ ID NO 89
<211> LENGTH: 23
<212> TYPE: RNA
<213> ORGANISM: Artificial Sequence
<220> FEATURE:
<223> OTHER INFORMATION: Synthetic Construct

<400> SEQUENCE: 89
caaagugcug uucgugcagg uag                                       23

<210> SEQ ID NO 90
<211> LENGTH: 21
<212> TYPE: RNA
<213> ORGANISM: Artificial Sequence
<220> FEATURE:
<223> OTHER INFORMATION: Synthetic Construct

<400> SEQUENCE: 90
ugagguagua gguuguauag u                                         21

<210> SEQ ID NO 91
<211> LENGTH: 21
<212> TYPE: RNA
<213> ORGANISM: Artificial Sequence
<220> FEATURE:
<223> OTHER INFORMATION: Synthetic Construct

<400> SEQUENCE: 91
uaaagugcug acagugcaga u                                         21

<210> SEQ ID NO 92
<211> LENGTH: 22
<212> TYPE: RNA
```

```
<213> ORGANISM: Artificial Sequence
<220> FEATURE:
<223> OTHER INFORMATION: Synthetic Construct

<400> SEQUENCE: 92
cagugcaaug augaaagggc au                                                22

<210> SEQ ID NO 93
<211> LENGTH: 23
<212> TYPE: RNA
<213> ORGANISM: Artificial Sequence
<220> FEATURE:
<223> OTHER INFORMATION: Synthetic Construct

<400> SEQUENCE: 93
uguaaacauc cuacacucuc agc                                               23

<210> SEQ ID NO 94
<211> LENGTH: 22
<212> TYPE: RNA
<213> ORGANISM: Artificial Sequence
<220> FEATURE:
<223> OTHER INFORMATION: Synthetic Construct

<400> SEQUENCE: 94
uguaaacauc cccgacugga ag                                                22

<210> SEQ ID NO 95
<211> LENGTH: 23
<212> TYPE: RNA
<213> ORGANISM: Artificial Sequence
<220> FEATURE:
<223> OTHER INFORMATION: Synthetic Construct

<400> SEQUENCE: 95
uaauacugcc ugguaaugau gac                                               23

<210> SEQ ID NO 96
<211> LENGTH: 19
<212> TYPE: RNA
<213> ORGANISM: Artificial Sequence
<220> FEATURE:
<223> OTHER INFORMATION: Synthetic Construct

<400> SEQUENCE: 96
gugcauugua guugcauug                                                    19

<210> SEQ ID NO 97
<211> LENGTH: 22
<212> TYPE: RNA
<213> ORGANISM: Artificial Sequence
<220> FEATURE:
<223> OTHER INFORMATION: Synthetic Construct

<400> SEQUENCE: 97
uagcagcacg uaaauauugg cg                                                22

<210> SEQ ID NO 98
<211> LENGTH: 21
<212> TYPE: RNA
<213> ORGANISM: Artificial Sequence
<220> FEATURE:
<223> OTHER INFORMATION: Synthetic Construct

<400> SEQUENCE: 98
ugagguagua gauuguauag u                                                 21
```

-continued

```
<210> SEQ ID NO 99
<211> LENGTH: 22
<212> TYPE: RNA
<213> ORGANISM: Artificial Sequence
<220> FEATURE:
<223> OTHER INFORMATION: Synthetic Construct

<400> SEQUENCE: 99
uagcagcaca ucaugguuua ca                                                  22

<210> SEQ ID NO 100
<211> LENGTH: 22
<212> TYPE: RNA
<213> ORGANISM: Artificial Sequence
<220> FEATURE:
<223> OTHER INFORMATION: Synthetic Construct

<400> SEQUENCE: 100
aaaccguuac cauuacugag uu                                                  22

<210> SEQ ID NO 101
<211> LENGTH: 22
<212> TYPE: RNA
<213> ORGANISM: Artificial Sequence
<220> FEATURE:
<223> OTHER INFORMATION: Synthetic Construct

<400> SEQUENCE: 101
uagcagcaca uaaugguuug ug                                                  22

<210> SEQ ID NO 102
<211> LENGTH: 23
<212> TYPE: RNA
<213> ORGANISM: Artificial Sequence
<220> FEATURE:
<223> OTHER INFORMATION: Synthetic Construct

<400> SEQUENCE: 102
agcagcauug uacagggcua uga                                                 23

<210> SEQ ID NO 103
<211> LENGTH: 23
<212> TYPE: RNA
<213> ORGANISM: Artificial Sequence
<220> FEATURE:
<223> OTHER INFORMATION: Synthetic Construct

<400> SEQUENCE: 103
ugugcaaauc uaugcaaaac uga                                                 23

<210> SEQ ID NO 104
<211> LENGTH: 21
<212> TYPE: RNA
<213> ORGANISM: Artificial Sequence
<220> FEATURE:
<223> OTHER INFORMATION: Synthetic Construct

<400> SEQUENCE: 104
aucguagagg aaaauccacg u                                                   21

<210> SEQ ID NO 105
<211> LENGTH: 22
<212> TYPE: RNA
<213> ORGANISM: Artificial Sequence
<220> FEATURE:
<223> OTHER INFORMATION: Synthetic Construct
```

-continued

```
<400> SEQUENCE: 105
aaagugcuuc ccuuuugugu gu                                      22

<210> SEQ ID NO 106
<211> LENGTH: 23
<212> TYPE: RNA
<213> ORGANISM: Artificial Sequence
<220> FEATURE:
<223> OTHER INFORMATION: Synthetic Construct

<400> SEQUENCE: 106
uauggcuuuu uauuccuaug uga                                     23

<210> SEQ ID NO 107
<211> LENGTH: 23
<212> TYPE: RNA
<213> ORGANISM: Artificial Sequence
<220> FEATURE:
<223> OTHER INFORMATION: Synthetic Construct

<400> SEQUENCE: 107
gaauguugcu cggugaaccc cuu                                     23

<210> SEQ ID NO 108
<211> LENGTH: 18
<212> TYPE: RNA
<213> ORGANISM: Artificial Sequence
<220> FEATURE:
<223> OTHER INFORMATION: Synthetic Construct

<400> SEQUENCE: 108
ucuacagugc acgugucu                                           18

<210> SEQ ID NO 109
<211> LENGTH: 22
<212> TYPE: RNA
<213> ORGANISM: Artificial Sequence
<220> FEATURE:
<223> OTHER INFORMATION: Synthetic Construct

<400> SEQUENCE: 109
caucaaagug gaggcccucu cu                                      22

<210> SEQ ID NO 110
<211> LENGTH: 21
<212> TYPE: RNA
<213> ORGANISM: Artificial Sequence
<220> FEATURE:
<223> OTHER INFORMATION: Synthetic Construct

<400> SEQUENCE: 110
aucacauugc caggauuuc c                                        21

<210> SEQ ID NO 111
<211> LENGTH: 21
<212> TYPE: RNA
<213> ORGANISM: Artificial Sequence
<220> FEATURE:
<223> OTHER INFORMATION: Synthetic Construct

<400> SEQUENCE: 111
uuugaaccau cacucgacuc c                                       21

<210> SEQ ID NO 112
<211> LENGTH: 22
<212> TYPE: RNA
```

```
<213> ORGANISM: Artificial Sequence
<220> FEATURE:
<223> OTHER INFORMATION: Synthetic Construct

<400> SEQUENCE: 112
uccuguacug agcugccccg ag                                              22

<210> SEQ ID NO 113
<211> LENGTH: 23
<212> TYPE: RNA
<213> ORGANISM: Artificial Sequence
<220> FEATURE:
<223> OTHER INFORMATION: Synthetic Construct

<400> SEQUENCE: 113
uacccuguag auccgaauuu gug                                             23

<210> SEQ ID NO 114
<211> LENGTH: 21
<212> TYPE: RNA
<213> ORGANISM: Artificial Sequence
<220> FEATURE:
<223> OTHER INFORMATION: Synthetic Construct

<400> SEQUENCE: 114
ugauugucca aacgcaauuc u                                               21

<210> SEQ ID NO 115
<211> LENGTH: 22
<212> TYPE: RNA
<213> ORGANISM: Artificial Sequence
<220> FEATURE:
<223> OTHER INFORMATION: Synthetic Construct

<400> SEQUENCE: 115
gaaguuguuc gugguggauu cg                                              22

<210> SEQ ID NO 116
<211> LENGTH: 23
<212> TYPE: RNA
<213> ORGANISM: Artificial Sequence
<220> FEATURE:
<223> OTHER INFORMATION: Synthetic Construct

<400> SEQUENCE: 116
agcagcauug uacagggcua uca                                             23

<210> SEQ ID NO 117
<211> LENGTH: 21
<212> TYPE: RNA
<213> ORGANISM: Artificial Sequence
<220> FEATURE:
<223> OTHER INFORMATION: Synthetic Construct

<400> SEQUENCE: 117
uuggucsccu ucaaccagcu a                                               21

<210> SEQ ID NO 118
<211> LENGTH: 22
<212> TYPE: RNA
<213> ORGANISM: Artificial Sequence
<220> FEATURE:
<223> OTHER INFORMATION: Synthetic Construct

<400> SEQUENCE: 118
cuccugacuc cagguccugu gu                                              22
```

-continued

<210> SEQ ID NO 119
<211> LENGTH: 22
<212> TYPE: RNA
<213> ORGANISM: Artificial Sequence
<220> FEATURE:
<223> OTHER INFORMATION: Synthetic Construct

<400> SEQUENCE: 119
ugagguagua gguugugugg uu                                          22

<210> SEQ ID NO 120
<211> LENGTH: 23
<212> TYPE: RNA
<213> ORGANISM: Artificial Sequence
<220> FEATURE:
<223> OTHER INFORMATION: Synthetic Construct

<400> SEQUENCE: 120
uggcaguguc uuagcugguu guu                                         23

<210> SEQ ID NO 121
<211> LENGTH: 22
<212> TYPE: RNA
<213> ORGANISM: Artificial Sequence
<220> FEATURE:
<223> OTHER INFORMATION: Synthetic Construct

<400> SEQUENCE: 121
uaauacugcc ggguaaugau gg                                          22

<210> SEQ ID NO 122
<211> LENGTH: 24
<212> TYPE: RNA
<213> ORGANISM: Artificial Sequence
<220> FEATURE:
<223> OTHER INFORMATION: Synthetic Construct

<400> SEQUENCE: 122
ucucacacag aaaucgcacc cguc                                        24

<210> SEQ ID NO 123
<211> LENGTH: 21
<212> TYPE: RNA
<213> ORGANISM: Artificial Sequence
<220> FEATURE:
<223> OTHER INFORMATION: Synthetic Construct

<400> SEQUENCE: 123
agagguagua gguugcauag u                                           21

<210> SEQ ID NO 124
<211> LENGTH: 22
<212> TYPE: RNA
<213> ORGANISM: Artificial Sequence
<220> FEATURE:
<223> OTHER INFORMATION: Synthetic Construct

<400> SEQUENCE: 124
uguaaacauc cccgacugga ag                                          22

<210> SEQ ID NO 125
<211> LENGTH: 22
<212> TYPE: RNA
<213> ORGANISM: Artificial Sequence
<220> FEATURE:
<223> OTHER INFORMATION: Synthetic Construct -continued

<400> SEQUENCE: 125
ugagaacuga auuccauggg uu 22